United States Patent
Teoh et al.

(10) Patent No.: US 10,478,192 B2
(45) Date of Patent: Nov. 19, 2019

(54) DETACHMENT MECHANISMS FOR IMPLANTABLE DEVICES

(71) Applicant: Boston Scientific Scimed, Inc., Maple Grove, MN (US)

(72) Inventors: Clifford Teoh, Los Altos, CA (US); Michael Williams, Oakland, CA (US); Gregory E. Mirigian, Dublin, CA (US); Kirsten Carroll, San Francisco, CA (US); James M. Anderson, Fridley, MN (US); Jay Rassat, Buffalo, MN (US); Benjamin Arcand, Minneapolis, MN (US); Derek Sutermeister, Eden Prairie, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 14/629,392

(22) Filed: Feb. 23, 2015

(65) Prior Publication Data
US 2017/0354419 A1    Dec. 14, 2017

Related U.S. Application Data

(63) Continuation of application No. 12/319,255, filed on Jan. 5, 2009, now abandoned.

(60) Provisional application No. 61/010,048, filed on Jan. 4, 2008.

(51) Int. Cl.
*A61B 17/12* (2006.01)

(52) U.S. Cl.
CPC .... *A61B 17/12022* (2013.01); *A61B 17/1214* (2013.01); *A61B 17/12109* (2013.01); *A61B 17/12113* (2013.01); *A61B 17/12145* (2013.01); *A61B 2017/1209* (2013.01); *A61B 2017/12068* (2013.01); *A61B 2017/12077* (2013.01)

(58) Field of Classification Search
CPC ........ A61B 17/12022; A61B 17/12145; A61B 17/12109; A61B 17/12113; A61B 17/1214; A61B 2017/1209; A61B 2017/12068; A61B 2017/12077
See application file for complete search history.

(56) References Cited

U.S. PATENT DOCUMENTS

| | | | | |
|---|---|---|---|---|
| 4,838,859 A | * | 6/1989 | Strassmann | A61B 1/00156 604/95.03 |
| 5,578,074 A | | 11/1996 | Mirigian | |
| 2002/0049389 A1 | * | 4/2002 | Abreu | A61B 3/1241 600/558 |
| 2007/0239191 A1 | * | 10/2007 | Ramzipoor | A61B 17/12022 606/191 |
| 2007/0299422 A1 | * | 12/2007 | Inganas | A61B 17/0057 604/508 |

(Continued)

FOREIGN PATENT DOCUMENTS

| | | |
|---|---|---|
| WO | 200106579 | 1/2001 |
| WO | 2004079832 | 9/2004 |
| WO | 2007130163 | 11/2007 |

*Primary Examiner* — Richard G Louis

(57) ABSTRACT

Disclosed herein are detachment mechanisms for vaso-occlusive devices that allow for rapid operator-controlled release of the vaso-occlusive device into the selected site. Also disclosed are vaso-occlusive assemblies comprising these detachment mechanisms and methods of using these detachment mechanisms and vaso-occlusive assemblies.

19 Claims, 34 Drawing Sheets

(56) References Cited

U.S. PATENT DOCUMENTS

2010/0063572 A1\* 3/2010 Teoh ................ A61B 17/12022
623/1.11

\* cited by examiner

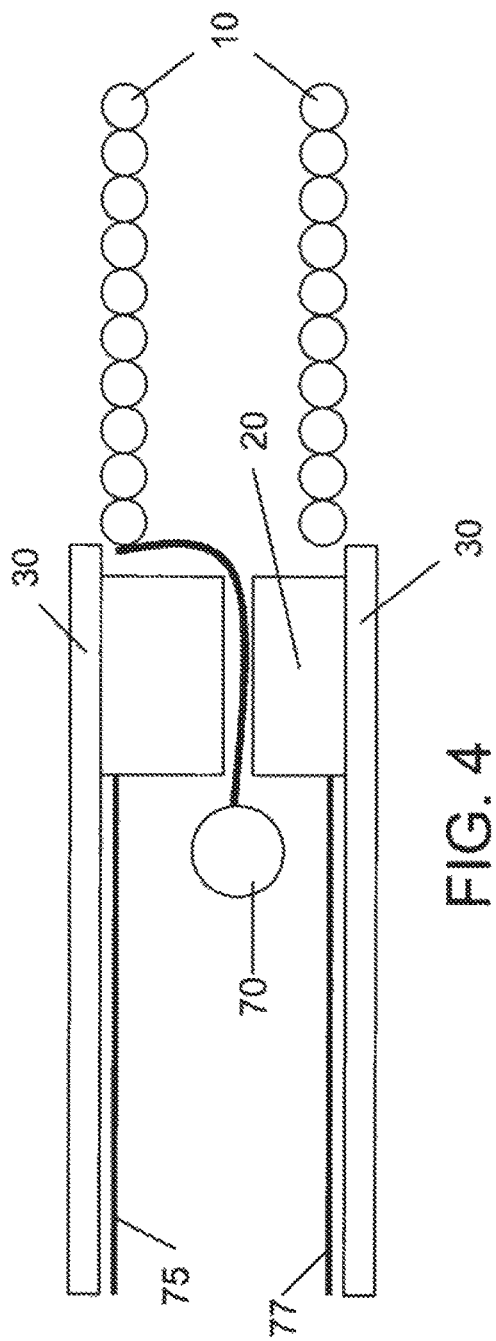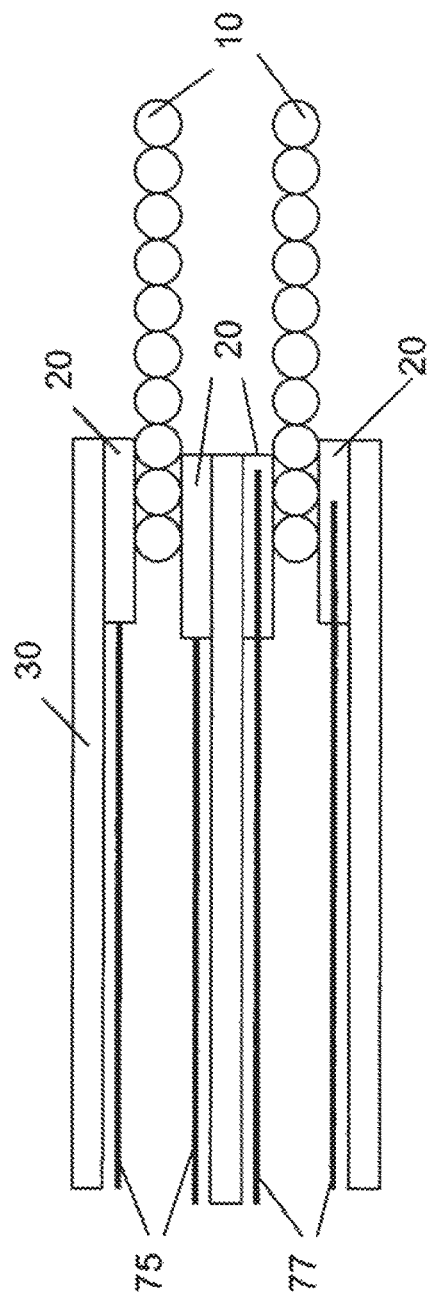
FIG. 4
FIG. 5

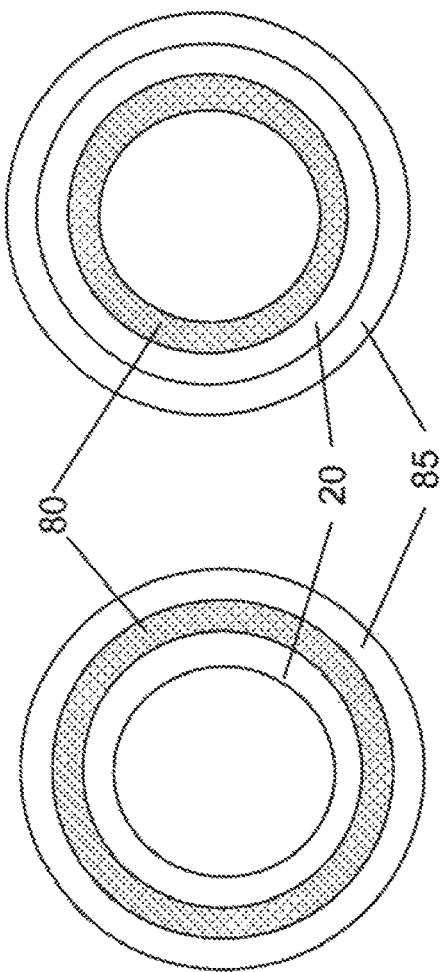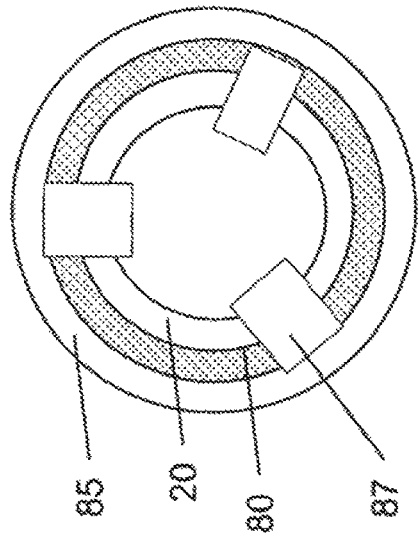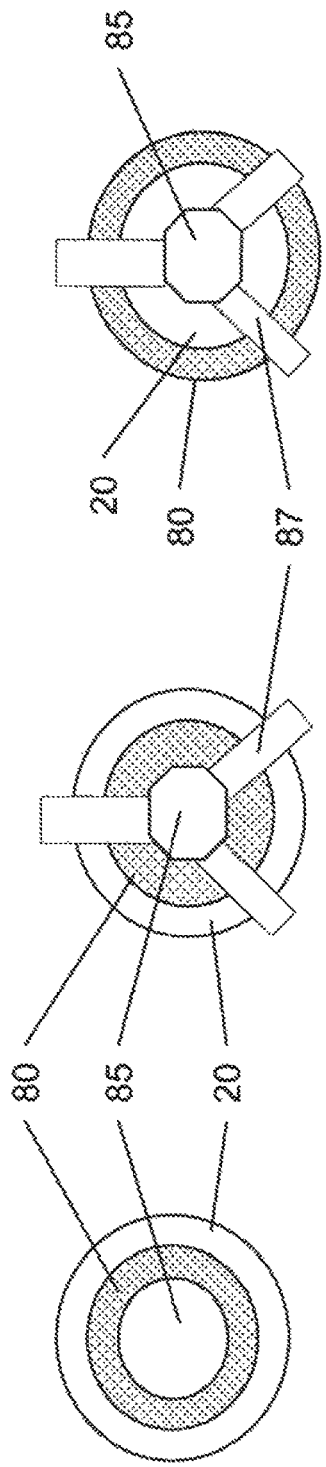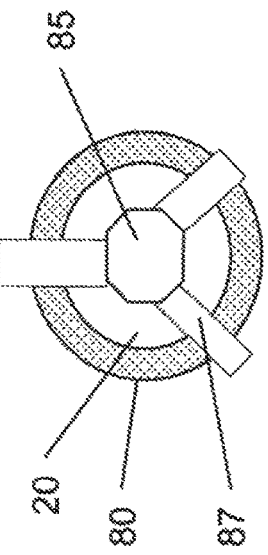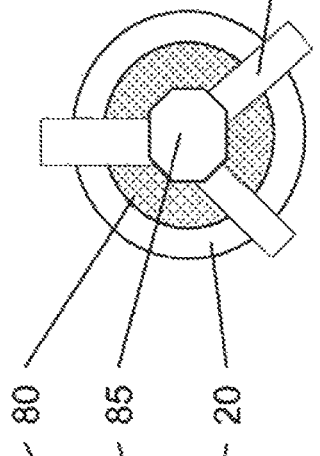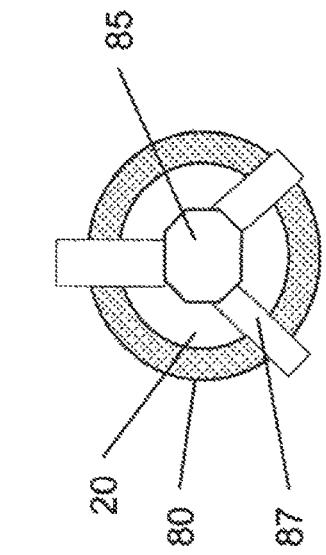

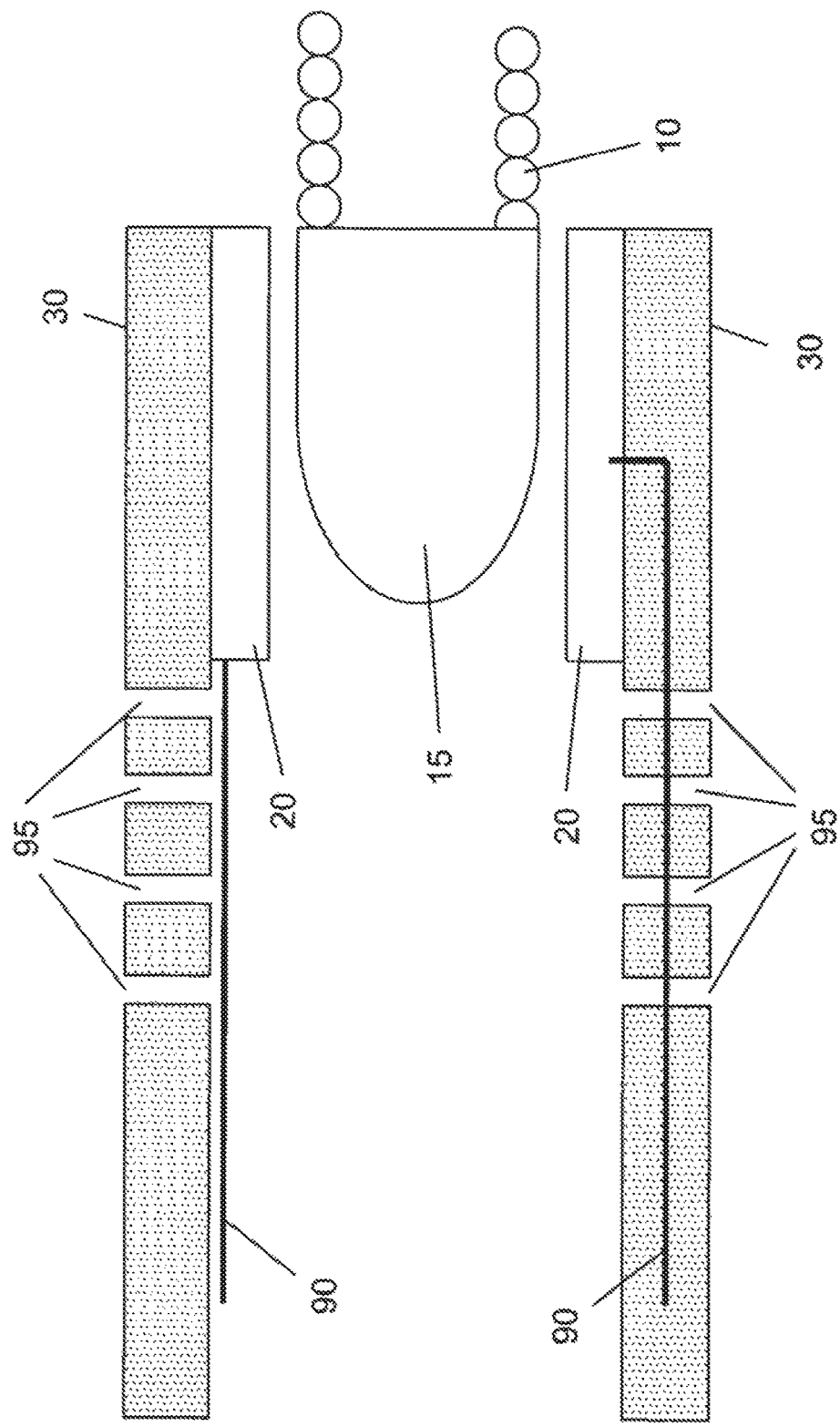

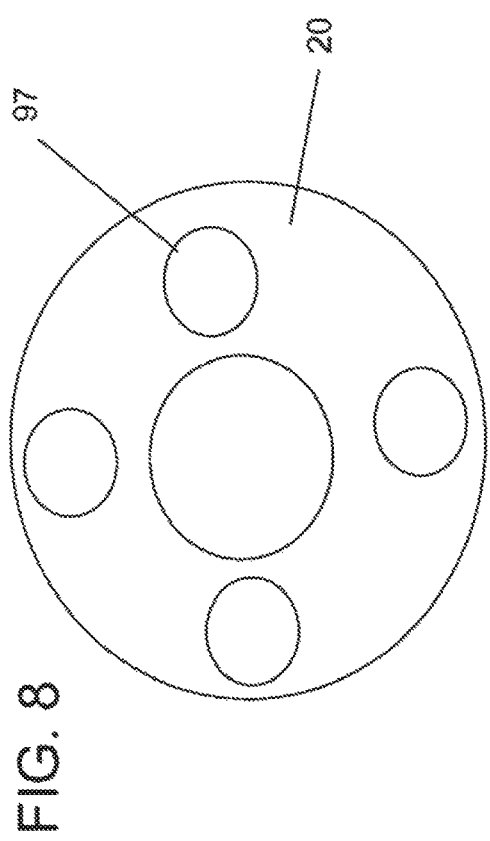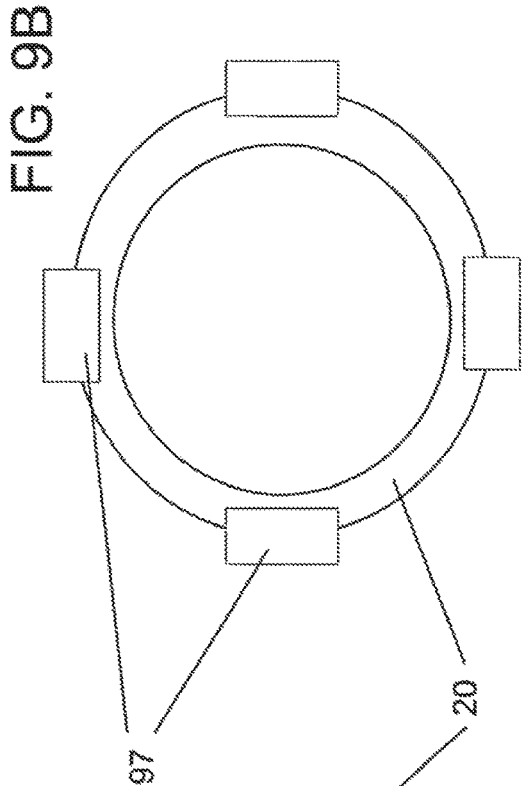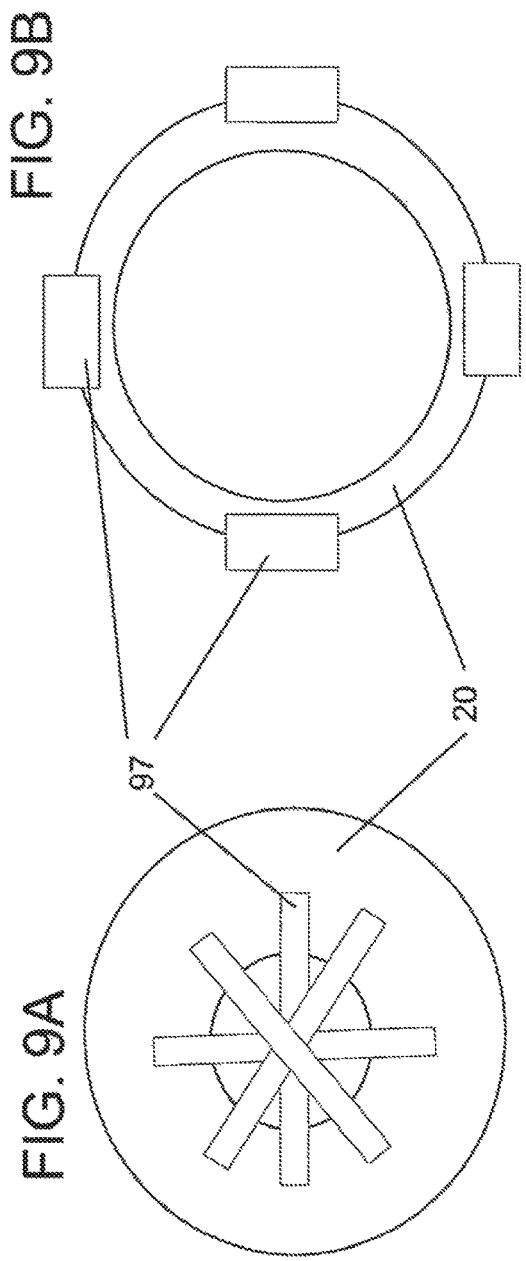

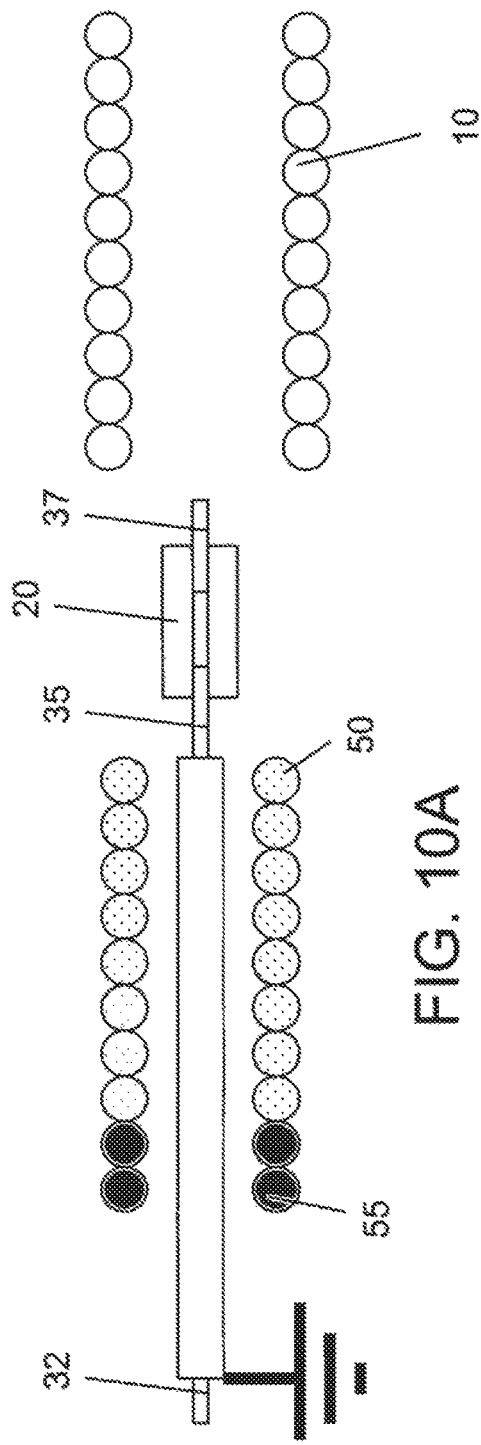
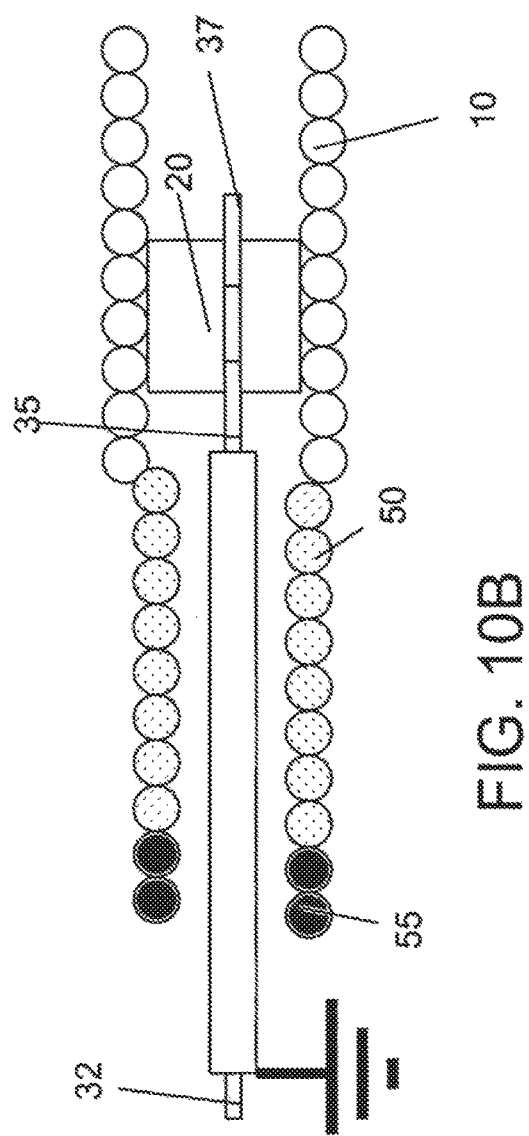

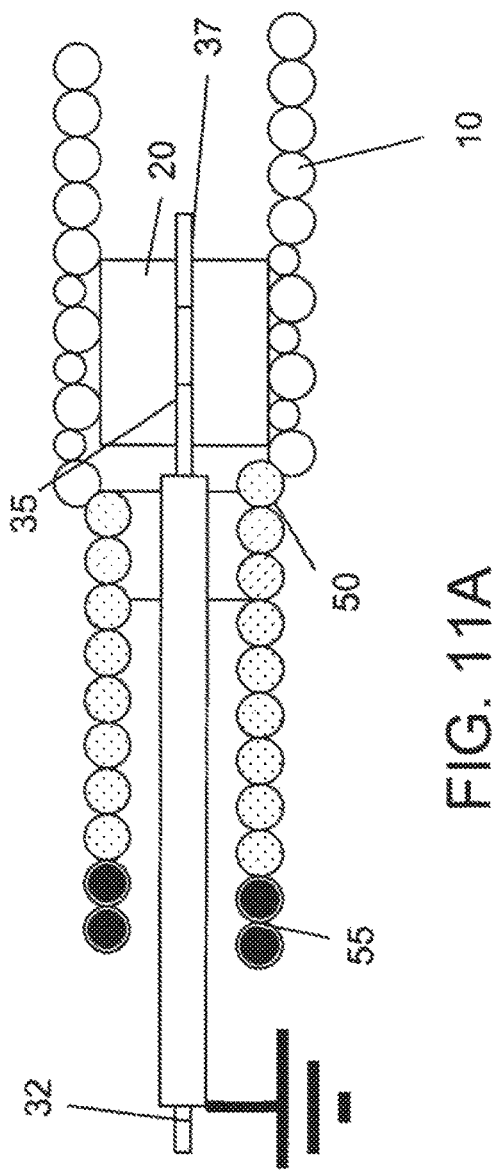
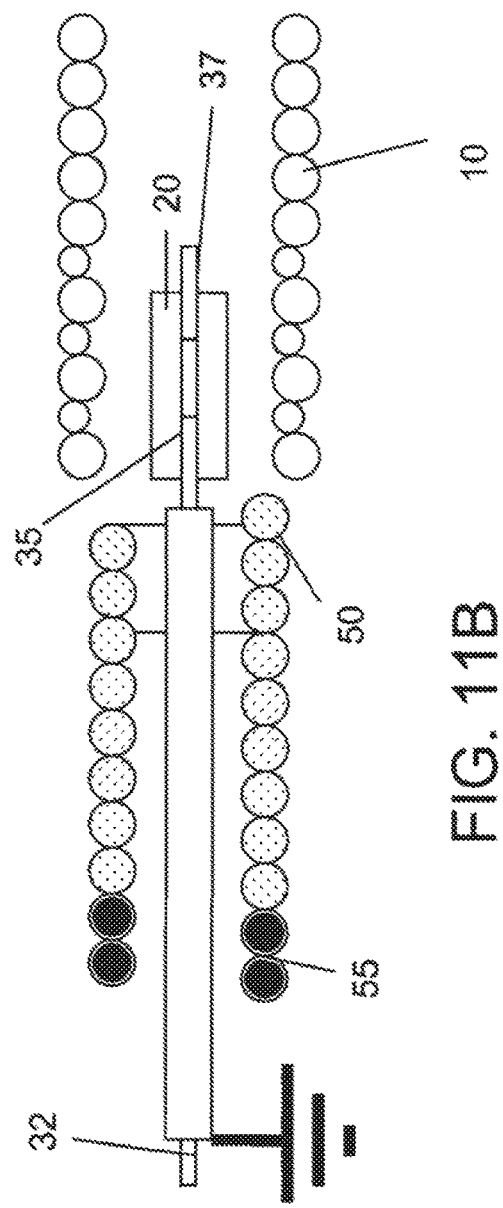
FIG. 11A
FIG. 11B

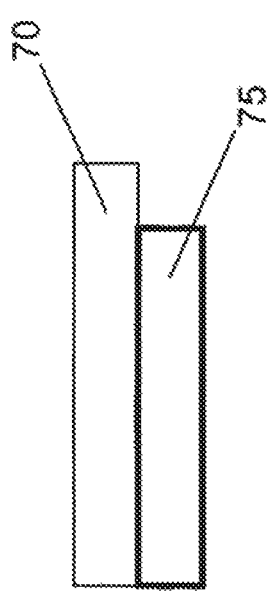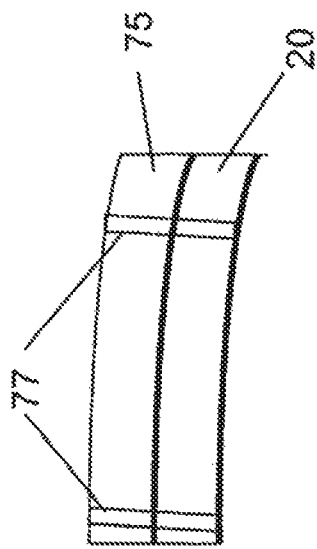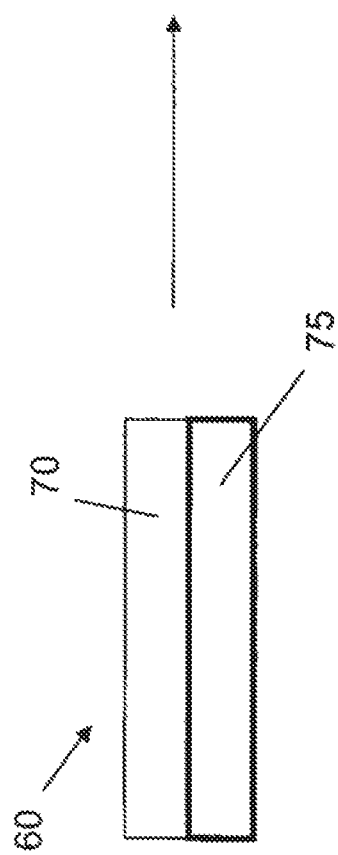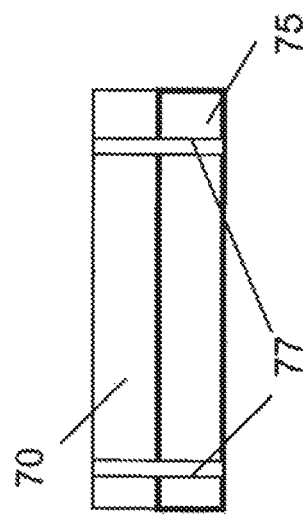

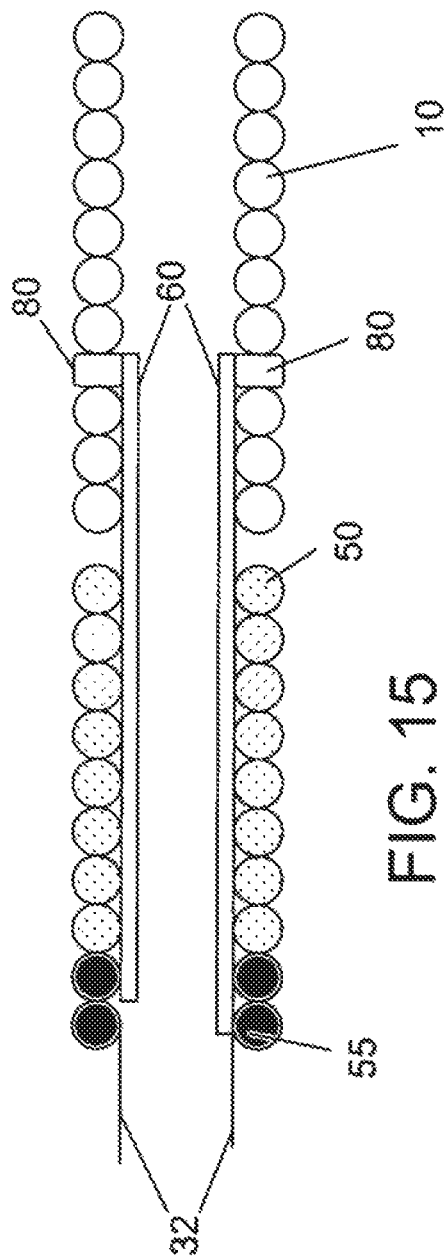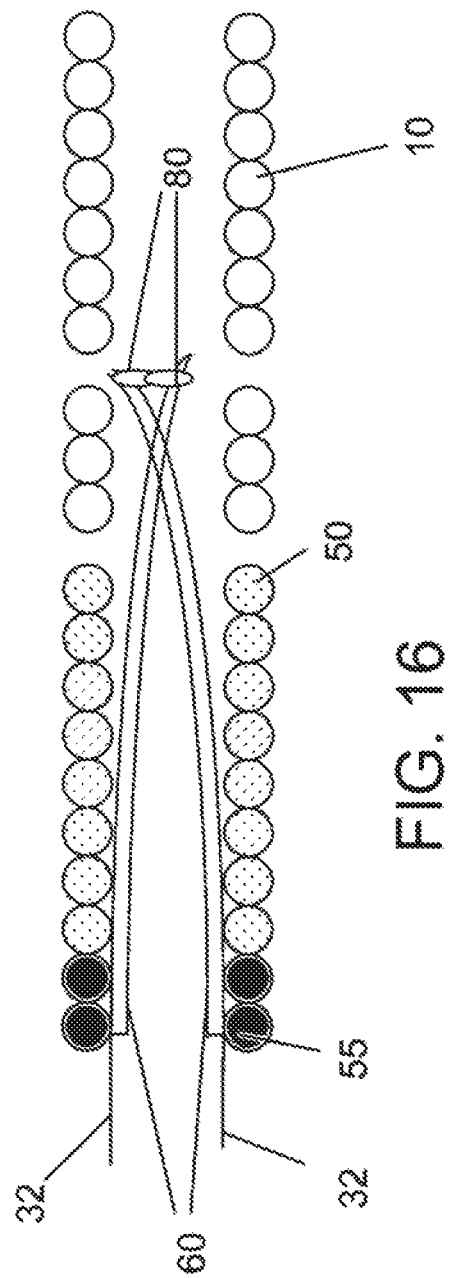

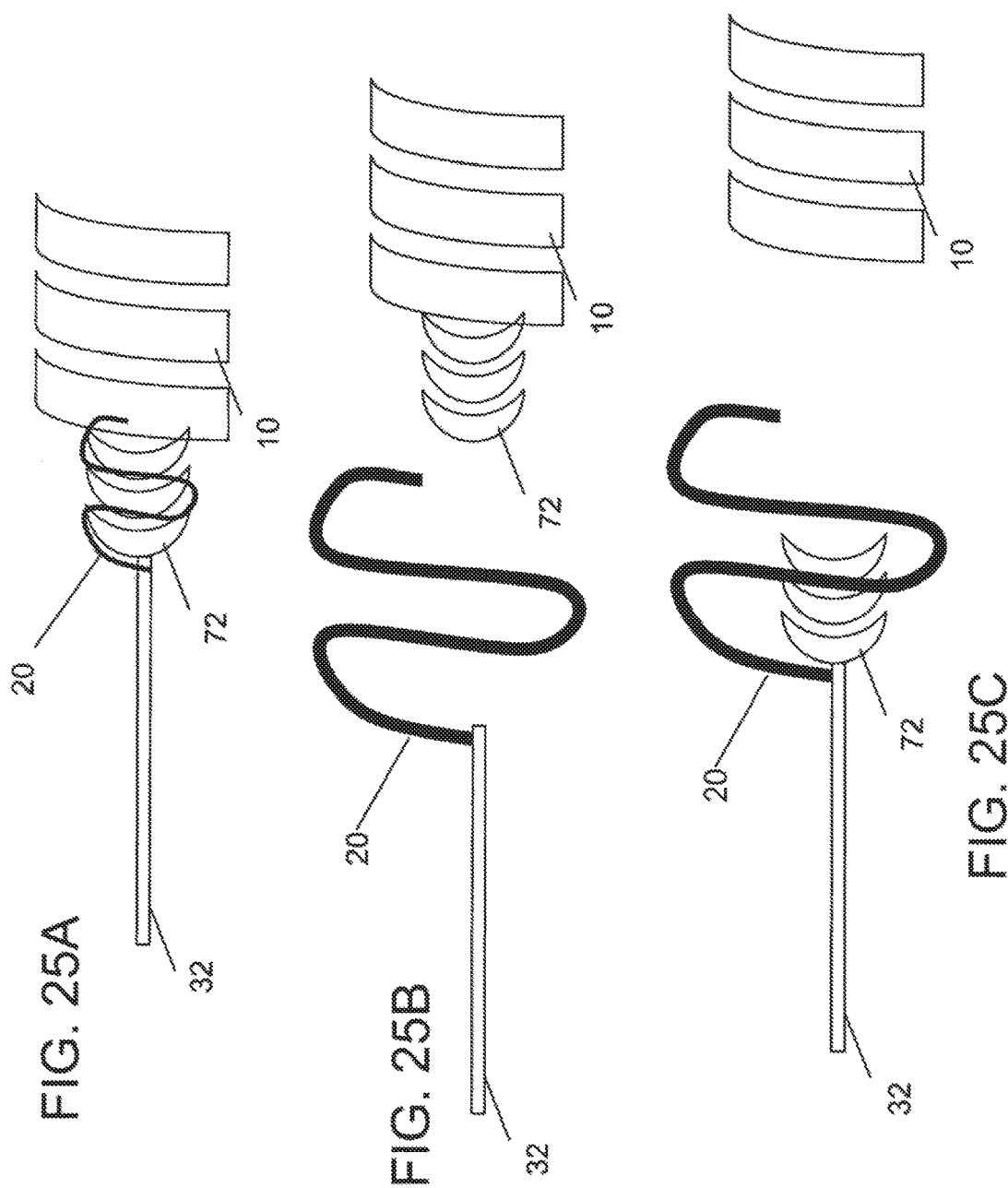

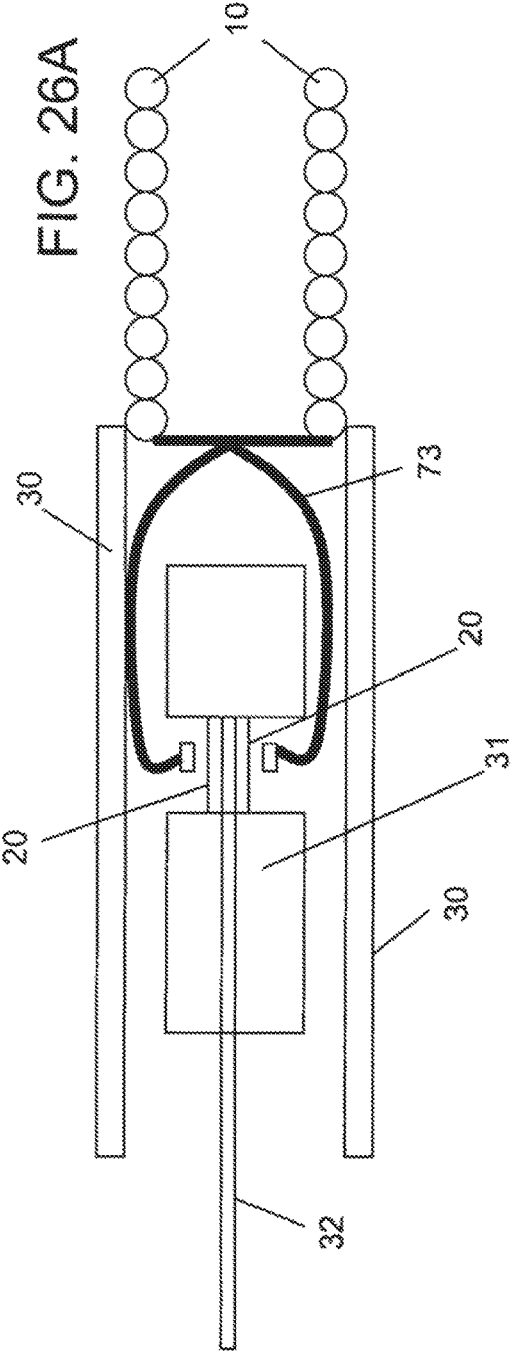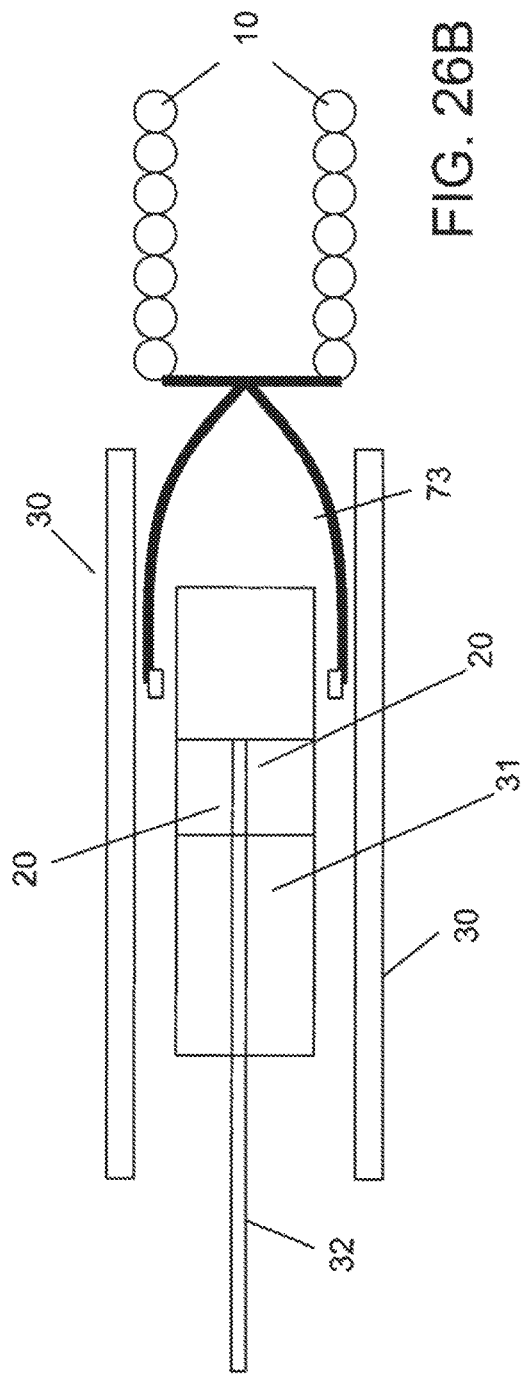

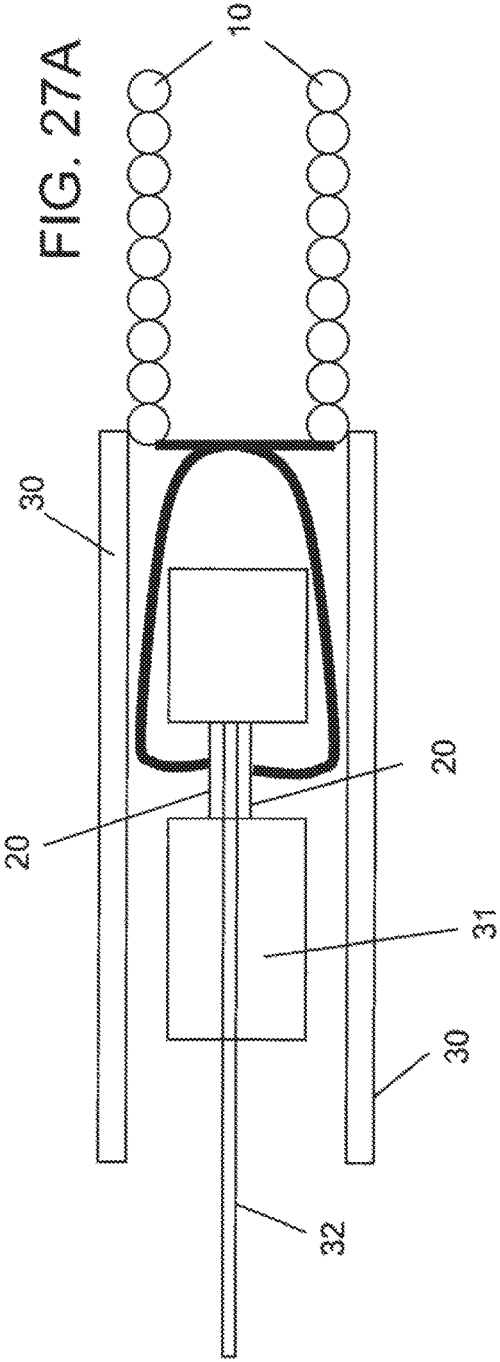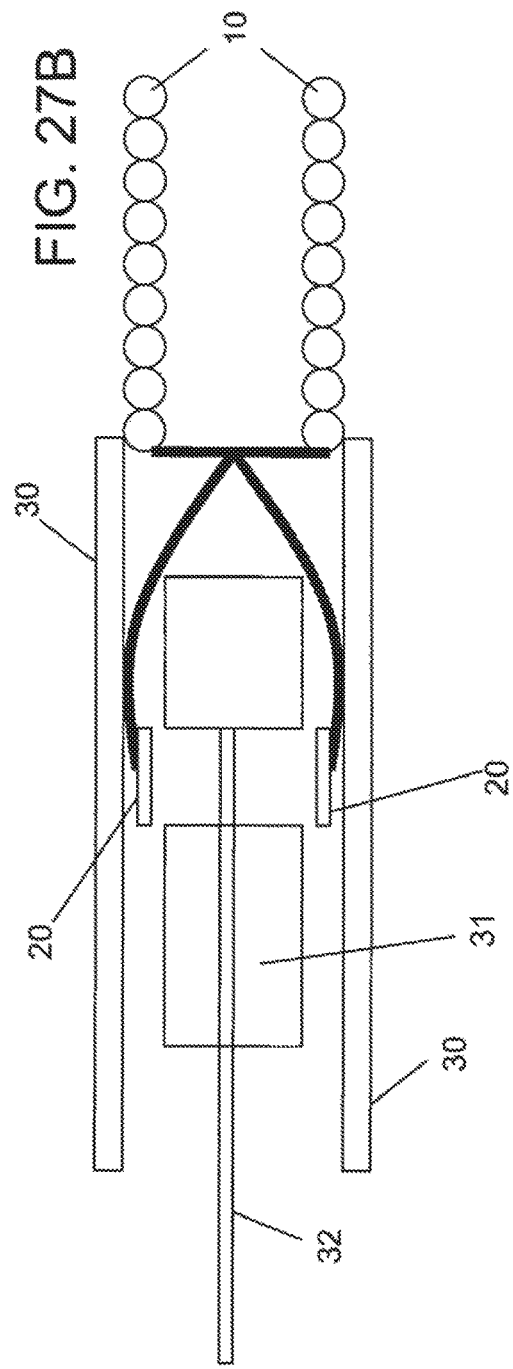

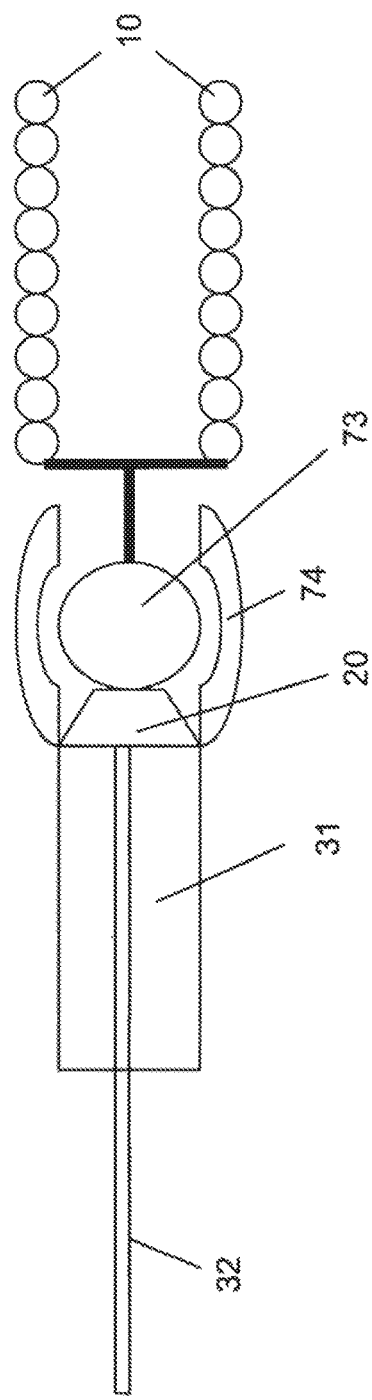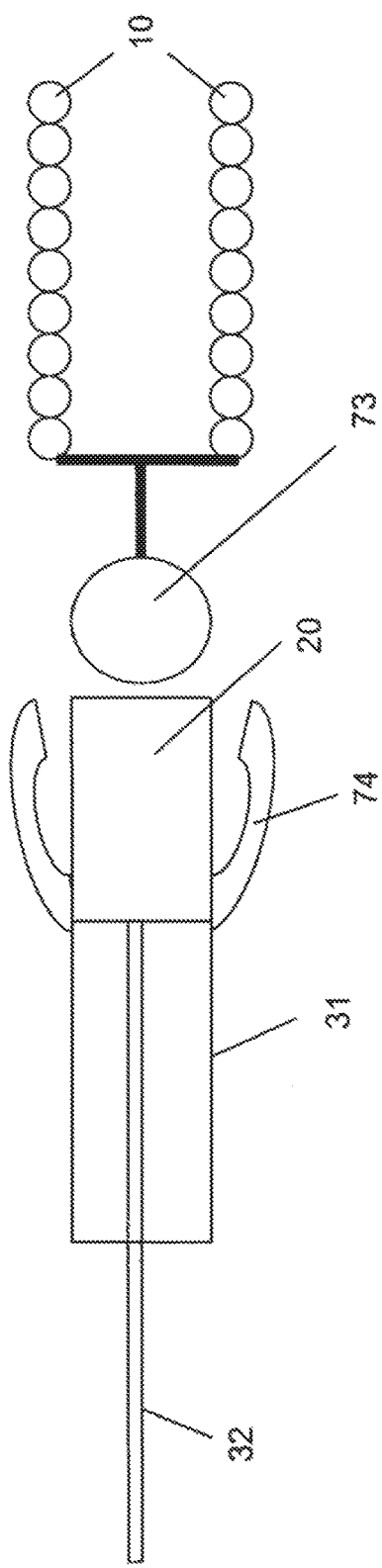

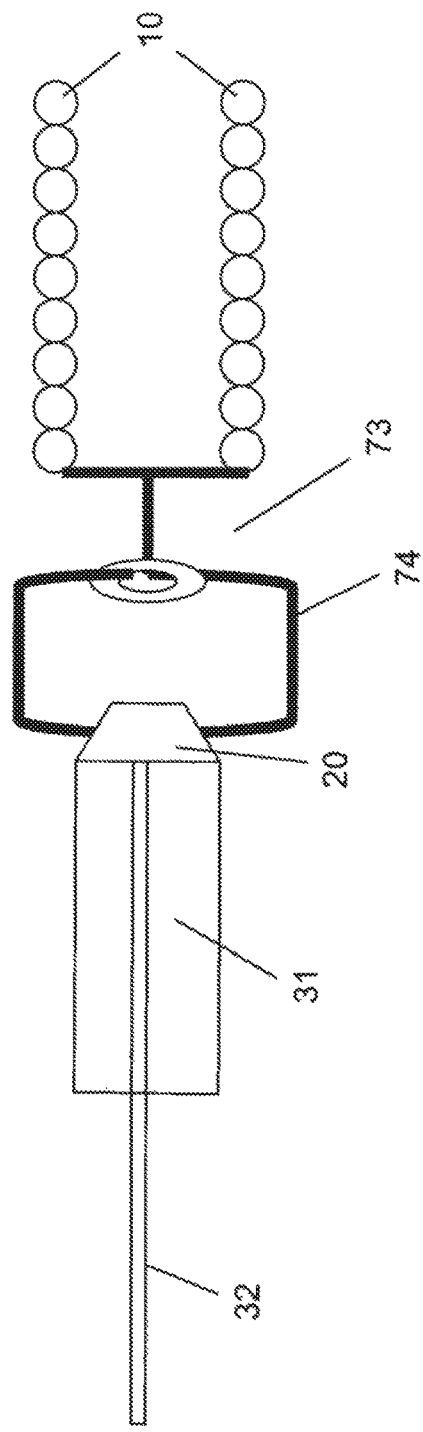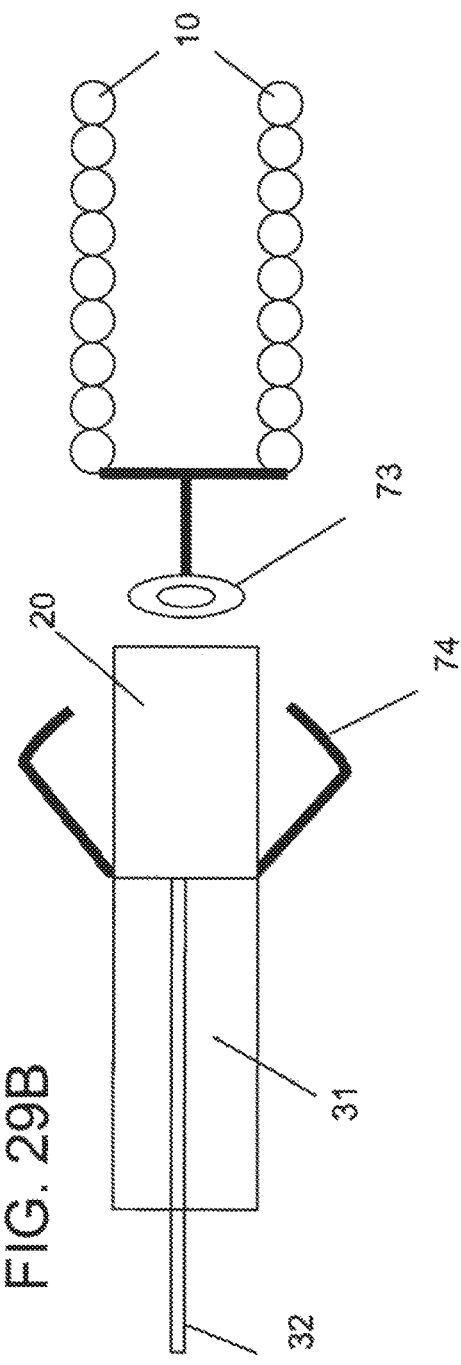

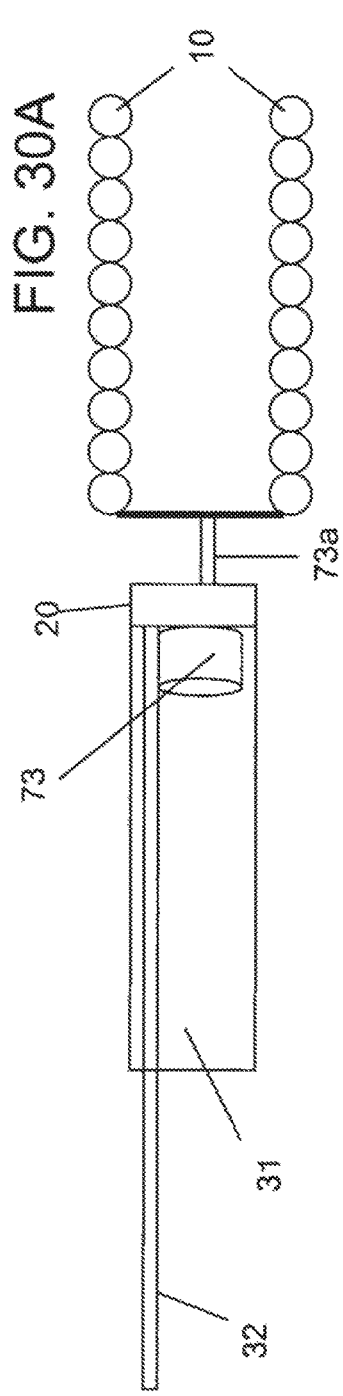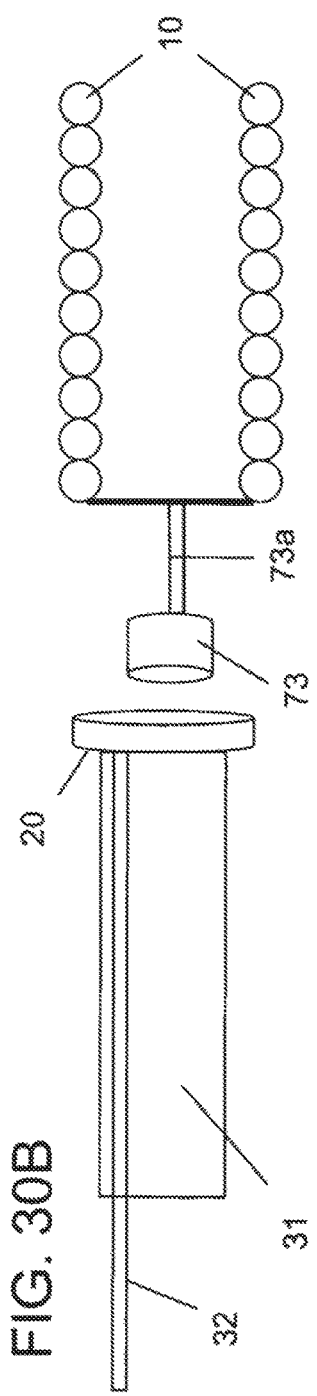

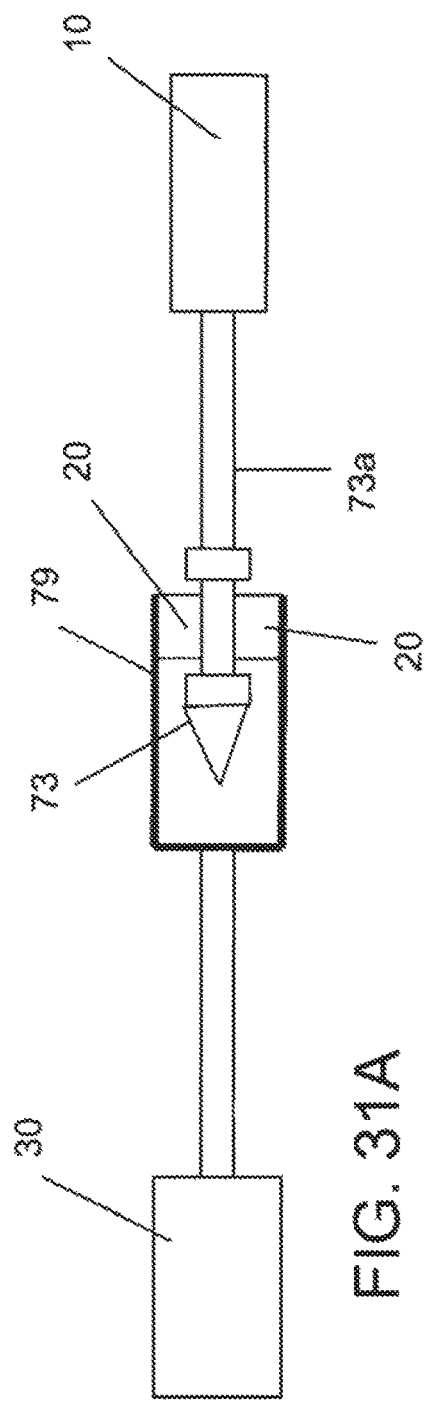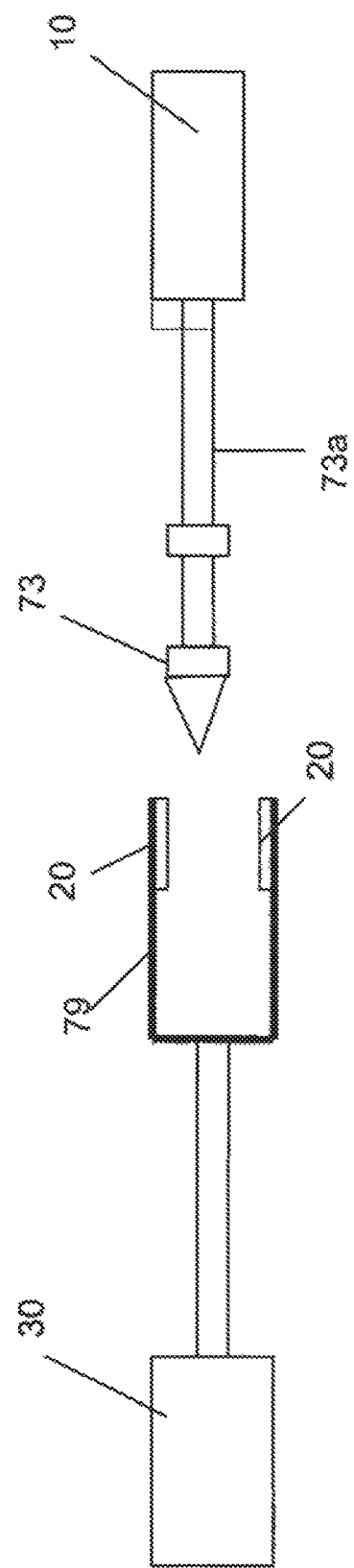

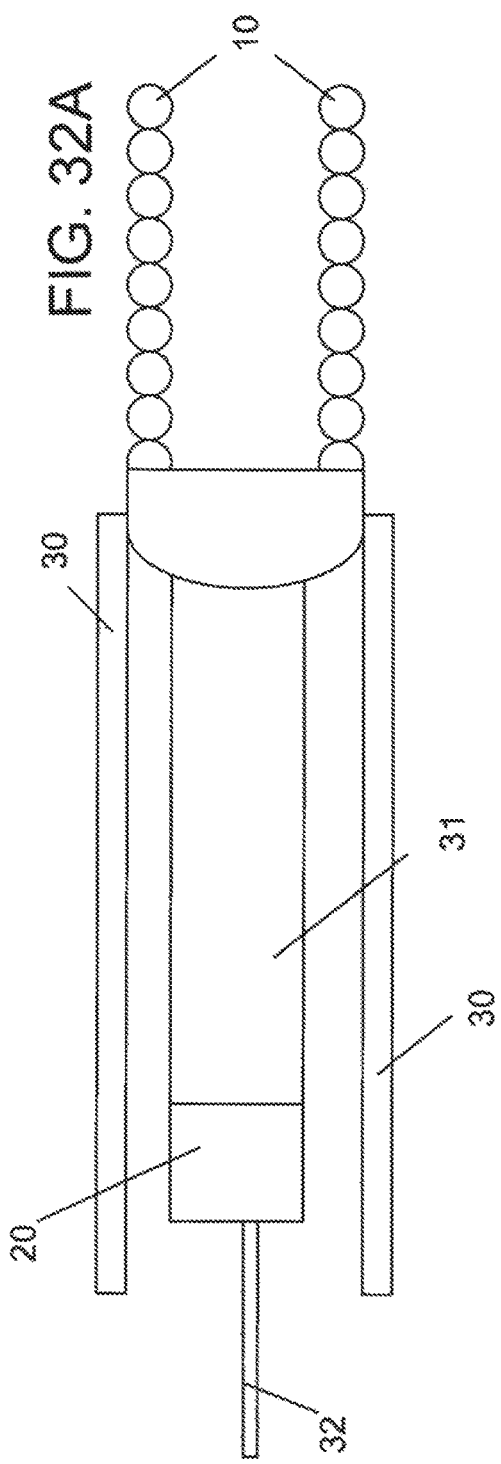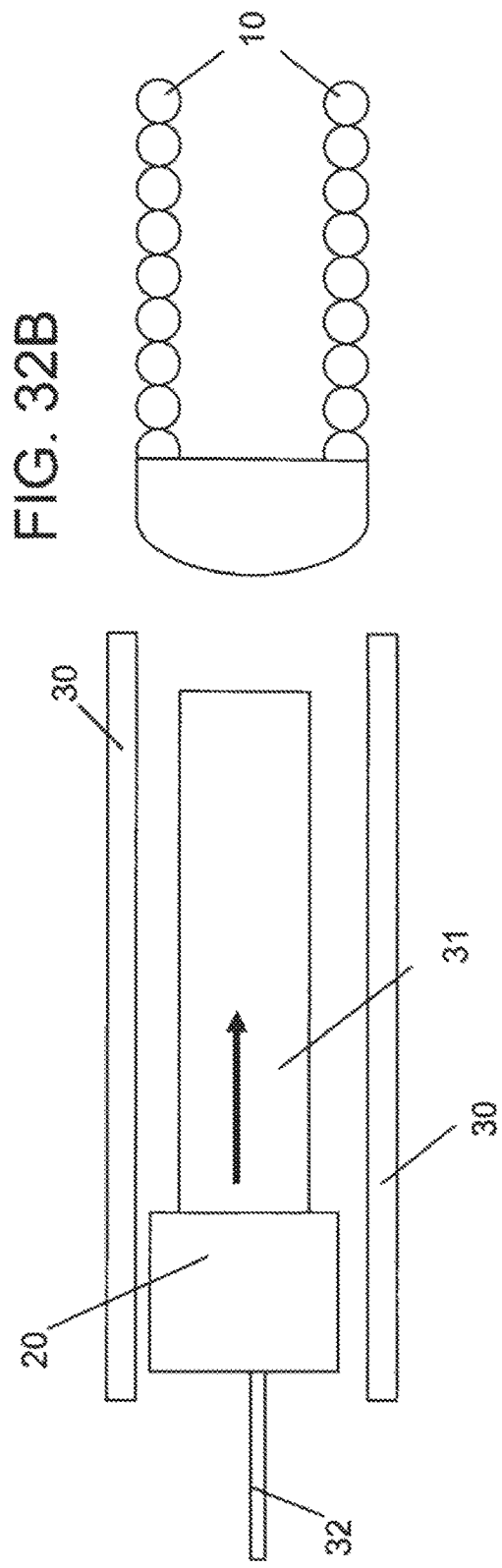

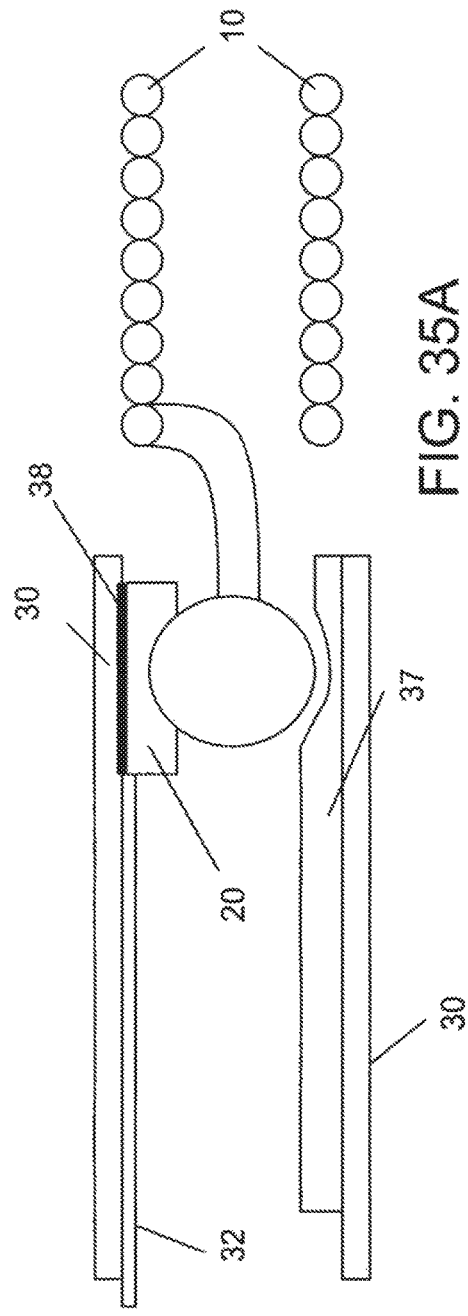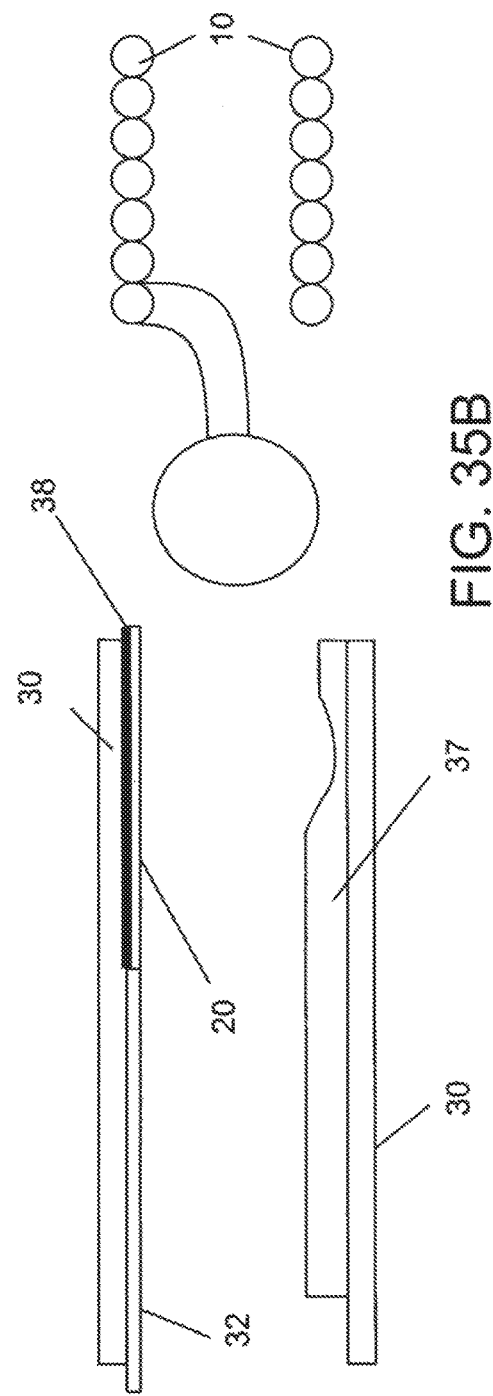

DETACHMENT MECHANISMS FOR IMPLANTABLE DEVICES

CROSS-REFERENCE TO RELATED APPLICATIONS

This application is a Continuation of U.S. patent application Ser. No. 12/319,255, filed Jan. 5, 2009, which claims the benefit of U.S. Provisional Application No. 61/010,048, filed Jan. 4, 2008, the disclosure of which is hereby incorporated by reference in its entirety.

TECHNICAL FIELD

Compositions and methods for implanting devices are described. In particular, detachment mechanisms that change configuration to deploy an implantable device such as an embolic device and assemblies comprising these detachment mechanisms are described.

BACKGROUND

Implantable devices are used for many indications including in the reproductive tract (e.g., uterine artery, fallopian occlusion), biliary implants and/or for peripheral and neurovasculature indications. For example, an aneurysm is a dilation of a blood vessel that poses a risk to health from the potential for rupture; clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of peripheral and neurovascular aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings that may be dimensioned to engage the walls of the vessels. (See, e.g., U.S. Pat. No. 4,994,069 to Ritchart et al.). Variations of such devices include polymeric coatings or attached polymeric filaments have also been described. See, e.g., U.S. Pat. Nos. 5,226,911; 5,935,145; 6,033,423; 6,280,457; 6,287,318; and 6,299,627. In addition, coil designs including stretch-resistant members that run through the lumen of the helical vaso-occlusive coil have also been described. See, e.g., U.S. Pat. Nos. 5,582,619; 5,833,705; 5,853,418; 6,004,338; 6,013,084; 6,179,857; and 6,193,728.

Coils have typically been placed at the desired site within the vasculature using a catheter and a pusher. The site is first accessed by the catheter (e.g., small diameter catheters such as those shown in U.S. Pat. Nos. 4,739,768 and 4,813,934). The catheter may be guided to the site through the use of guide-wires (see U.S. Pat. No. 4,884,579) or by flow-directed means such as balloons placed at the distal end of the catheter.

Once the site has been reached, the catheter lumen is cleared by removing the guidewire (if a guidewire has been used), and one or more coils are placed into the proximal open end of the catheter and advanced through the catheter with a pusher. Once the coil reaches the distal end of the catheter, it is discharged from the catheter by the pusher into the vascular site. However, there are concerns when discharging the coil from the distal end of the catheter. For example, the plunging action of the pusher and the coil can make it difficult to position the coil at the site in a controlled manner and with a fine degree of accuracy. Inaccurate placement of the coil can be problematic because once the coil has left the catheter, it is difficult to reposition or retrieve the coil.

Several techniques involving Interlocking Detachable Coils (IDCs), which incorporate mechanical release mechanisms and Guglielmi Detachable Coils (GDCs), which utilize electrolytically actuated release mechanisms, have been developed to enable more accurate placement of coils within a vessel.

Electrolytic coil detachment is disclosed in U.S. Pat. Nos. 5,122,136; 5,354,295; 6,620,152; 6,425,893; and 5,976,131, all to Guglielmi et al., describe electrolytically detachable embolic devices. U.S. Pat. No. 6,623,493 describes vaso-occlusive member assembly with multiple detaching points. U.S. Pat. Nos. 6,589,236 and 6,409,721 describe assemblies containing an electrolytically severable joint. The coil is bonded via a metal-to-metal joint to the distal end of the pusher. The pusher and coil are made of dissimilar metals. The coil-carrying pusher is advanced through the catheter to the site and a small electrical current is passed through the pusher-coil assembly. The current causes the joint between the pusher and the coil to be severed via electrolysis. The pusher may then be retracted leaving the detached coil at an exact position within the vessel. Since no significant mechanical force is applied to the coil during electrolytic detachment, highly accurate coil placement is readily achieved. In addition, the electric current may facilitate thrombus formation at the coil site. The disadvantage of this method is that the electrolytic release of the coil may require a period of time that may inhibit rapid detachment of the coil from the pusher.

There is a need to provide alternative mechanisms for delivering implants, such as embolic coils, that allow for both accurate positioning of the implantable device and rapid detachment from the delivery device.

SUMMARY

Disclosed herein are detachment mechanisms for implantable devices, as well as assemblies comprising the detachment mechanisms and implantable devices. Methods of making and using these detachment mechanisms and assemblies are also provided.

In one aspect, provided herein is a detachment mechanism for an implantable device, the implantable device optionally having a lumen therein, the detachment mechanism comprising: at least one material that changes configuration upon application of heat or electrical energy, wherein the change in configuration releases the implantable device, and further wherein if the material extends into the optional lumen of the implantable device, the material directly contacts at least a portion the implantable device defining the lumen. Thus, if the material extends into the lumen of the device, the material is in direct contact with the interior surface of the implantable device. In certain embodiments, the change in configuration comprises a reduction in diameter and/or volume of the material. In other embodiments, the change in configuration comprises an expansion in diameter and/or volume of the material. In still other embodiments, the change in configuration comprises a deflection of the detachment mechanism.

In certain aspects, the detachment mechanisms described herein comprise an electroactive polymer and/or a metal or polymer, for example the electroactive polymer may be layered onto the metal or polymer.

In other aspects, the detachment mechanisms described herein comprise a layered strip of two or more metals of dissimilar thermal coefficients. In certain embodiments, the layered strip is wound into a spiral shape.

In any of the detachment mechanisms described herein, the material may directly contact a source of electric or heat energy. Furthermore, any of the detachment mechanisms described herein may directly engage the vaso-occlusive device. In addition, the detachment mechanism may contact a structure attached to the implantable device.

In another aspect, described herein is a detachment mechanism adapted to detachably engage a vaso-occlusive device, the detachment mechanism comprising an element that changes configuration upon application of electrical current or heat; and means for applying electrical current or heat to the change the configuration of the element.

In yet another aspect, provided herein is a vaso-occlusive assembly comprising a vaso-occlusive device; any of the detachment mechanisms described herein; and a source of electrical current or a heat source in contact with the detachment mechanism. In certain embodiments, the vaso-occlusive device comprises a helically wound vaso-occlusive coil. In still further embodiments, the vaso-occlusive assembly may further comprise a delivery mechanism, for example, a delivery mechanism comprising a stopper element.

In a still further aspect, described herein is a method of at least partially occluding an aneurysm, the method comprising the steps of introducing any of the vaso-occlusive assemblies described herein into the aneurysm, wherein the detachment mechanism engages the vaso-occlusive device; and changing the configuration of the detachment mechanism by applying or removing electrical current or thermal energy such that the detaching mechanism releases the vaso-occlusive device into the aneurysm.

These and other embodiments will readily occur to those of skill in the art in light of the disclosure herein.

BRIEF DESCRIPTION OF THE FIGURES

FIG. 3, panels FIG. 3A shows such an assembly when the electroactive polymer engages the vaso-occlusive device. FIG. 3B shows the assembly of FIG. 3A upon changing the configuration of the polymer to increase the length and reduce thickness of the polymer. FIG. 3C shows an intermediate de-energized state, which allows the delivery device to function as a coil pusher.

FIG. 4 is a cross-section, side-view of yet another exemplary assembly as described herein and shows a variation in which a structural element is attached to the distal end of the vaso-occlusive device to engage the electroactive polymer in one configuration and which, in the second configuration, releases the structure and, accordingly, the vaso-occlusive device.

FIG. 5 is a cross-section, side-view of yet another exemplary assembly as described herein and shows a design having two (inner and outer) layers of electroactive polymer.

FIG. 6, panels FIG. 6A to FIG. 6F, are cross-sections of exemplary configurations showing layering of electroactive polymer, filler material and core material, with or without slots.

FIG. 7 is a cross-section, side-view of an exemplary assembly as described herein including a delivery device with one or more apertures in the sidewalls.

FIG. 8 is a cross-section view of an exemplary electroactive polymer configuration that includes apertures (pores) in the electroactive polymer.

FIG. 9, panels FIG. 9A and FIG. 9B are cross-section views of additional exemplary electroactive polymer configurations. FIG. 9A shows an embodiment that includes slots in the electroactive polymer. FIG. 9B shows a ring shaped electroactive polymer with channels in the outer layer.

FIG. 10, panels FIG. 10A and FIG. 10B, are partial cross-section, side views depicting an exemplary assembly as described herein comprising an electroactive polymer that contracts upon activation with electrical current. FIG. 10A shows the assembly when electric current is applied to the electroactive polymer, which contracts to release the embolic coil. FIG. 10B shows the assembly in the un-activated in which the electroactive polymer is in an expanded configuration that engages the embolic coil.

FIG. 11, panels FIG. 11A and FIG. 11B, are partial cross-section, side views of another exemplary embodiment in which the electroactive polymer is in an expanded configuration upon activation with electrical current. FIG. 11A shows the assembly in the activated (engaged) configuration and FIG. 11B shows contraction of the electroactive polymer in the un-activated configuration (when electrical current is removed).

FIG. 12, panels FIG. 12A and FIG. 12B, are overviews of a bi-layered strip of materials where each layer responds differently to the application of electrical current or heat. FIG. 12A shows an exemplary strip prior to application of heat or electrical current. FIG. 12B shows dissimilar expansion of the disparate layers upon application of heat or electrical current.

FIG. 13, panels FIG. 13A and FIG. 13B, are overviews of a bi-layered strip used in detachment mechanisms as described herein. FIG. 13A shows the bi-layer strip prior to application of heat or electrical current. FIG. 13B shows deflection of the strip upon application of heat of electrical current due to the dissimilar thermal and/or electrical response characteristics of the layers.

FIG. 14, panels FIG. 14A shows the strip in the unengaged position. FIG. 14B shows the strip when engaged with the inner surface of the lumen of the implantable device.

FIG. 15 is a cross-section view of an exemplary detachment mechanism comprising bilayer strips extending into the lumen of the implantable embolic coil and contacting the inner surface of the embolic coil. The strips are shown in the configuration in which they engage spaces in the winds of the embolic coil.

FIG. 16 is a cross-section view of the exemplary detachment mechanism of FIG. 15 shown in the configuration in which they deflect toward each other and no longer engage the coil.

FIG. 25, panels FIG. 25A to FIG. 25C, are side-views showing an exemplary variation in which a detachment mechanism comprising an electroactive polymer is attached to a structure on the proximal end of the implantable device. The unexpanded configuration, the electroactive polymer engages the structure and in the expanded configuration releases the structure and deploys the implantable device.

FIG. 26, panels FIG. 26A and FIG. 26B, are cross-section, side-views showing an exemplary variation in which the implantable device engages a pusher element when the electroactive polymer is in the contracted position. FIG. 26B depicts how, upon expansion of electroactive polymer, the implantable device is released.

FIG. 27, panels FIG. 27A to FIG. 27D, are cross-section showing an exemplary variation in which the implantable device engages a pusher element via a ring shaped electroactive polymer. FIG. 27A shows the electroactive polymer ring in the engaged (unexpanded) configuration and FIG. 27B shows linear expansion of the electroactive polymer ring which releases the ring from the pusher element. FIG. 27C shows an electroactive polymer ring structure made of multiple linearly-expanding elements in an unexpanded configuration and FIG. 27D shows the ring of FIG. 27C after linear expansion of the electroactive polymer elements.

FIG. 28, panels FIG. 28A and FIG. 28B, are cross-section, side-views showing another exemplary variation in which the implantable device engages a pusher element via a ball joint when the electroactive polymer is in the contracted position (FIG. 28A). Upon expansion of the electroactive polymer, the implantable device is released (FIG. 28B).

FIG. 29, panels FIG. 29A and FIG. 29B, are cross-section, side-views showing another exemplary variation in which the implantable device engages a pusher element via arms through a ring structure when the electroactive polymer is in the contracted position. Upon expansion of the electroactive polymer, implantable device is released.

FIG. 30, panels FIG. 30A to FIG. 30D, show an embodiment where the unexpanded electroactive polymer engages an implantable coil and pusher element via a structure extending from the proximal end of the coil. FIG. 30A is a cross-section side-view of the assembly with the electroactive polymer in the unexpanded position. FIG. 30B is a cross-section, side-view of the assembly with the electroactive polymer in the expanded position.

FIG. 30C is a top view of the structure extending from the implantable coil and electroactive polymer in unexpanded configuration. FIG. 30D is a top view of the structure shown in FIG. 30C with the electroactive polymer in the expanded configuration.

FIG. 31, panels FIG. 31A and FIG. 31B, show a variation including an electroactive polymer coupling receiver in which the structure extending from the implantable device is engaged in the coupling receiver when the electroactive polymer is in the expanded configuration (FIG. 31A) and which releases the implantable device when the electroactive polymer is in the unexpanded configuration (FIG. 31B).

FIG. 32, panels FIG. 32A and FIG. 32B, show an electroactive polymer activated compression (e.g., hydraulic) detachment mechanism. FIG. 32A shows the assembly when the electroactive polymer is in the unexpanded configuration and FIG. 32B shows the same assembly after expansion of the electroactive polymer.

FIG. 33, panels

FIG. 34, panels

FIG. 35, panels FIG. 35A and FIG. 35B, are cross-section, side-views showing another exemplary variation in which the implantable device includes a proximal ball structure which is engaged in the delivery device by the electroactive polymer in an expanded position (FIG. 35A). Upon contraction of the electroactive polymer, the implantable device is released (FIG. 35B).

DETAILED DESCRIPTION

Figure 1:
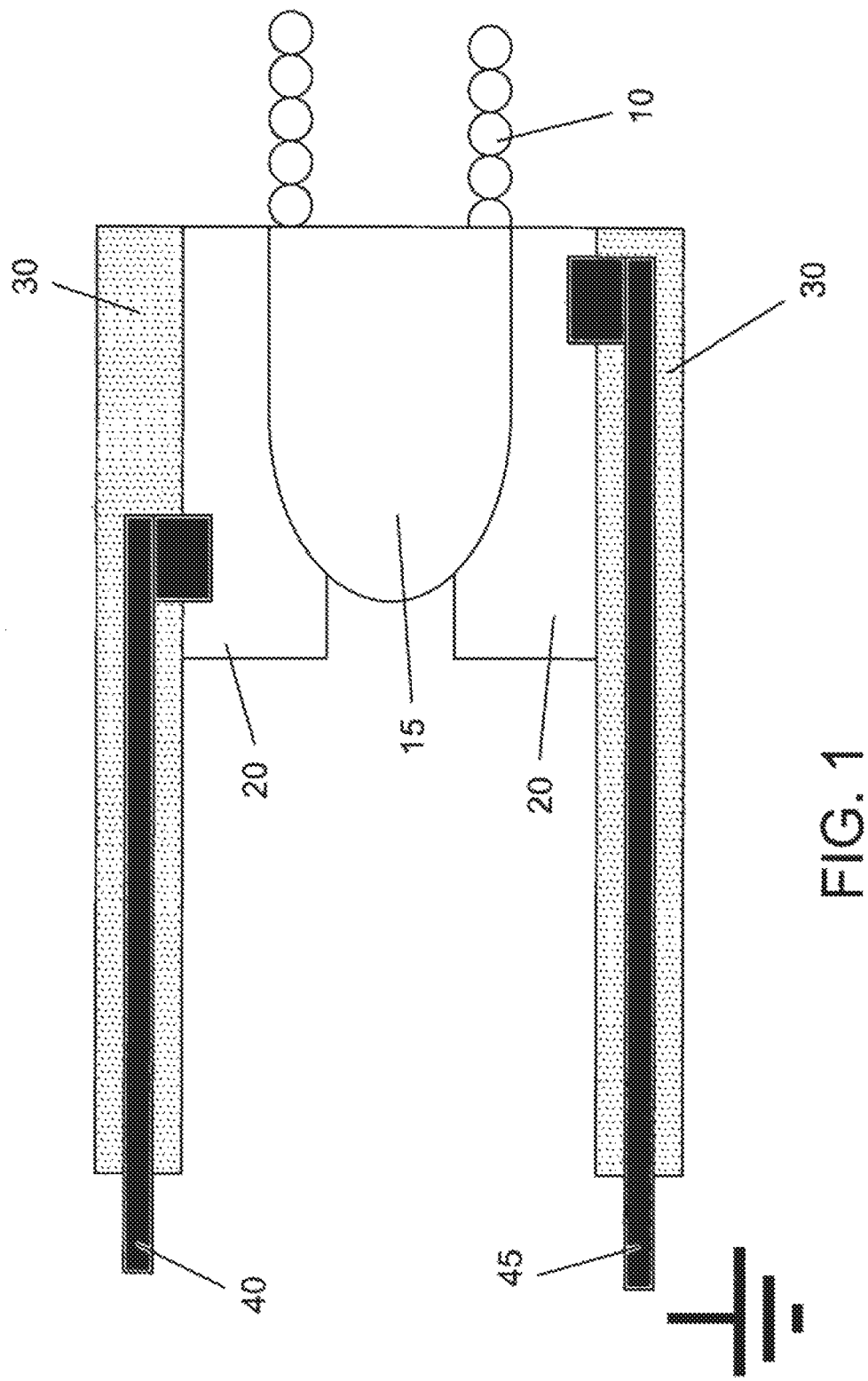
FIG. 1 is a partial cross-section, side view depicting an exemplary vaso-occlusive assembly as described herein. The electroactive polymer is shown in the configuration in which it engages the vaso-occlusive device to be delivered.

Detachment mechanisms for implantable devices, including occlusive (e.g. embolic) devices, and assemblies are described. The detachment mechanisms described herein can be utilized in devices useful in vascular and neurovascular indications and are useful in delivering embolic devices to aneurysms, for example small-diameter, curved or otherwise difficult to access vasculature, for example aneurysms, such as cerebral aneurysms. Methods of making and using these detachments and assemblies comprising these detachments are also aspects of this disclosure.

Currently, the gold-standard method of delivering implantable vaso-occlusive devices is via electrolytic detachment (e.g., GDC coils). While electrolytic detachment solves the drawbacks of earlier mechanical detachments (e.g., the need for the mechanism to be fully inside the catheter in order to remain engaged), electrolytically detachable coils typically require approximately 20-30 seconds detachment times.

The detachment mechanisms described herein that allow for rapid and precise detachment of an implantable device upon application of electrical energy and/or heat. Advantages of the present disclosure include, but are not limited to, (i) the provision of rapidly detachable vaso-occlusive devices; (ii) the provision of mechanically detachable implantable devices that can be extended beyond the catheter tip, thereby allowing for more precise placement of the devices; and (iii) the provision of occlusive devices that minimize the mechanical motion needed to detach the devices.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to a device comprising "an electroactive polymer" includes devices comprising of two or more such materials or multiple layers of the same electroactive polymer.

The detachment mechanisms described herein allow for rapid release of the vaso-occlusive device from the delivery mechanism. By "rapid" release is meant release in less than 30 seconds, preferably less than 20 seconds and even more preferably between 1 and 15 seconds (e.g., 1, 2, 3, 4, 5, 6, 7, 8, 9, 10, 11, 12, 13, 14 or 15 seconds).

The detachment mechanism may take any desired shape. The detachment mechanism may engage the implantable device by contacting the exterior of the device, directly (e.g., the exterior of the device) or indirectly (e.g., via a structure in contact with the exterior of the device). However, unlike previously described electroactive detachment mechanisms for implantable devices, when the detachment extends into the lumen of the implantable device, it directly engages the interior surface of the device (in either the activated or inactivated state, depending on the properties of the selected materials). The detachment mechanism may be shaped into a ring or spiral structure, for example a spiral wound from a bilayer strip.

In certain aspects, the detachment mechanism comprises an electroactive polymer (EAP) that changes configuration upon the application to electrical energy. Any electroactive polymer can be used, so long as it changes configuration sufficiently in response to application of current. Multiple electroactive polymers may be used, for example, in layers and/or admixed together. Non-limiting examples of suitable electroactive polymers include polypyrrole, nafion, polyanilene, polythiofene and the like. See, e.g., U.S. Pat. No. 6,933,659 and U.S. Patent Publication 20040182704. Electroactive polymers may expand or contract upon activation.

In certain embodiments, the change in configuration of the electroactive polymer(s) is such that, upon the application of electrical current, the polymer's diameter is reduced and, optionally, the axial length is increased. Thus, in the absence of electrical current, the detachment mechanism engages the implantable device within the delivery device. This allows that the delivery-detachment mechanism and vaso-occlusive device to be moved as a unit, even when the implantable device is secured by the electroactive polymer such that extends from the distal end of the delivery mechanism (e.g., delivery catheter or delivery tube). When electricity is applied, the electroactive polymer changes configuration (contracts) such that it no longer secures the device to the delivery device. Accordingly, upon application of electricity to the device is rapidly released into the selected site. In these embodiments, the unactivated electroactive polymer provides a physical compressive grip on the implantable device (e.g., on the exterior or interior surface and/or on a structure affixed to the proximal end of the implantable device) until electrical current is used to active the detachment mechanism. These "fail safe" embodiments minimize the possibility of false or premature detachment of the coil and are advantageous in the event of power failure or accidental interruption so that the embolic remains attached to the delivery wire.

Alternatively, the electroactive polymer may be such that its diameter increases upon application of electrical current. In these embodiments, electrical energy would be applied during deployment and release of the implantable device achieved by stopping the application of electrical current when the implantable device is in the desired position. In embodiments in which the electroactive polymer expands upon the application of electrical energy, the implantable device is positioned within the delivery device and the electroactive polymer is energized to keep the coil in the desired position. The device is then introduced into the access delivery device (e.g., microcatheter). Upon achieving the desired positioning within the aneurysm, the coil is detached by de-energizing the electroactive polymer. These embodiments allow the option of the supplying long lengths of uncut embolic coils to the surgeon. The surgeon can trim the coils to the desired length and mount them on the delivery device to deploy the coils. Delivery devices can be reused multiple times so long as the lumen remains sufficiently clear for insertion.

Detachment mechanisms comprising an electroactive polymer may further comprise metal (e.g., nitinol, stainless steel) and/or polymeric materials. In certain embodiments, the detachment mechanism comprises a super-elastic metal alloy such as nitinol which allows for durability and flexibility. Stainless steel or other metals or alloys can also be used. A portion or all of the detachment mechanism may include one or more surface treatments (coating, machining, microtexturing, etc.). The electroactive polymer is typically coated onto the surface of the metal and/or polymericmaterial.

In other embodiments, the detachment mechanism comprises two or more materials (e.g., metals and/or polymers), typically in layers. Furthermore, in response to thermal or electrical energy, the two or more materials of the detachment mechanism change configuration differently. For example, in certain embodiments, the detachment mechanism comprises a bilayer strip of an electroactive polymer coated onto a metal or polymer substrate. In other embodiments, metals or polymers that respond differently when activated by thermal or electrical energy are employed. The detachment mechanisms described herein also allow for ready retrieval and/or repositioning of vaso-occlusive devices.

Suitable delivery devices include delivery catheters (e.g., microcatheters) with or without delivery tubes (hypotubes) therein. When included, hypotubes may extend the length for the delivery catheter or may be only at the distal region. The delivery devices may include one or more apertures in the side walls that allow for inflow and outflow of electrolytes. See, also, U.S. Provisional Patent Application No. 60/930,436, entitled "Catheters for Electrolytically Detachable Embolic Devices," filed May 16, 2007. In any of the embodiments described herein, the delivery device may be slotted or spiral cut to reduce bending stiffness while maintaining axial controllability.

In certain embodiments, a braided delivery tube, for example comprising electrodes or heat conducting elements embedded in the sidewalls or extending through the lumen of the delivery tube is employed. Such delivery tubes are adapted to be delivered through conventional catheters (e.g. microcatheters) and, when extended from the distal end of the catheter, allow for even more accurate positioning of the implantable device prior to detachment. In other embodiments, the electrodes (bi-polar or unipolar) extend through the part or all of the lumen of the delivery device.

Furthermore, as noted above, electrical or thermal energy can be provided to the detachment mechanism in any suitable way. The energy source can directly contact the detachment mechanism, for example using a delivery mechanism (e.g., catheter or delivery tube) comprising electrodes or heat conductors in the side-walls. See, e.g., U.S. Pat. Nos. 6,059,779 and 7,020,516. In addition, the electrodes can be attached to a core wire. For example, bi-polar electrodes and/or anodes alone or twisted with a core wire cathode can also be used to supply current to the electroactive polymer. Optionally, the leads may be secured to the core wire; for example via adhesives or via heat-shrink polymer lamination such as PTFE, PEP, PET or urethane. The conductive element may include a polymer jacket/liner to insulate the electrical leads and/or reduce friction during advancement. Alternatively, the detachment mechanism can be activated to change configuration indirectly via a conductive material (e.g., metal) that transmits the electrical or thermal energy to the detachment junction.

It will be apparent that one or more of the electrodes and/or conductive materials that transmit electrical energy to the electroactive polymer may include insulating coatings (e.g., polyimide or the like). For electrical energy, alternating or direct current may be used. Preferably, direct current is used. The amount of current applied will vary according to the application although typically less than 4 volts, preferably around 2 volts is applied to activate the electroactive polymer of the detachment mechanism. Likewise, for materials that change configuration in response to thermal energy, heat can be applied as desired by the operator to change the configuration of the detachment mechanism.

In certain embodiments, the conductor and/or electrodes are distal to the distal end of the delivery mechanism (e.g., tube or coil stopper). As shown in the Figures, the detachment mechanism may be disposed over the conductive surfaces, for example by physical expansion over the electrodes/heat conductors, heat shrinking, conductive adhesives, or the like.

The detachment mechanisms described herein can be adapted to be used with any implantable device, including, but not limited to, vaso-occlusive devices, fallopian tube occlusive devices, uterine implantable devices, biliary implantable devices and the like. The devices may be metal and/or polymeric. Suitable metals and metal alloys include the Platinum Group metals, especially platinum, rhodium, palladium, rhenium, as well as tungsten, gold, silver, tantalum, and alloys of these metals. The core element may also comprise of any of a wide variety of stainless steels. Very desirable materials of construction, from a mechanical point of view, are materials that maintain their shape despite being subjected to high stress including but not limited to "superelastic alloys" such as nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol."

The detachment mechanisms described herein may be used with implantable devices of any structure, for example, devices of tubular structures, for examples, braids, coils, combination braid and coils and the like. Thus, although depicted in the Figures described below as a vaso-occlusive coil, the device may be of a variety of shapes or configuration including, but not limited to, braids, knits, woven structures, tubes (e.g., perforated or slotted tubes), cables, injection-molded devices and the like. See, e.g., U.S. Pat. No. 6,533,801 and International Patent Publication WO 02/096273. The implantable device may change shape upon deployment, for example change from a constrained linear form to a relaxed, three-dimensional (secondary) configuration. See, also, U.S. Pat. No. 6,280,457. In a preferred embodiment, the core element comprises a metal wire wound into a primary helical shape. The core element may be, but is not necessarily, subjected to a heating step to set the wire into the primary shape. Methods of making vaso-occlusive coils having a linear helical shape and/or a different three-dimensional (secondary) configuration are known in. the art and described in detail in the documents cited above, for example in U.S. Pat. No. 6,280,457. Thus, it is further within the scope of this disclosure that the vaso-occlusive device as a whole or elements thereof comprise secondary shapes or structures that differ from the linear coil shapes depicted in the Figures, for examples, spheres, ellipses, spirals, ovoids, figure-8 shapes, etc. The devices described herein may be self-forming in that they assume the secondary configuration upon deployment into an aneurysm. Alternatively, the devices may assume their secondary configurations under certain conditions (e.g., change in temperature, application of energy, etc.).

FIG. 1 shows a partial cross-section, side-view of an exemplary detachable vaso-occlusive assembly as described herein in a configuration in which the electroactive polymer engages the vaso-occlusive device within delivery device. In this position, the electroactive polymer 20 engages the proximal region of vaso-occlusive coil 10, namely tip ball 15 of the vaso-occlusive coil 10. Electrodes 40, 45 extend through sidewall of delivery tube 30 and contact electroactive polymer 20. For electroactive polymers that contract upon application of electrical current, FIG. 1 shows the assembly in the un-activated state, where the electroactive polymer creates a lumen having an inner diameter (ID) smaller than the outer diameter (OD) of the embolic coil, allowing it to hold the coil in place. For electroactive polymers that expand upon application of electrical current, FIG. 1 shows the assembly in the activated state, again holding the coil in place.

Figure 2:
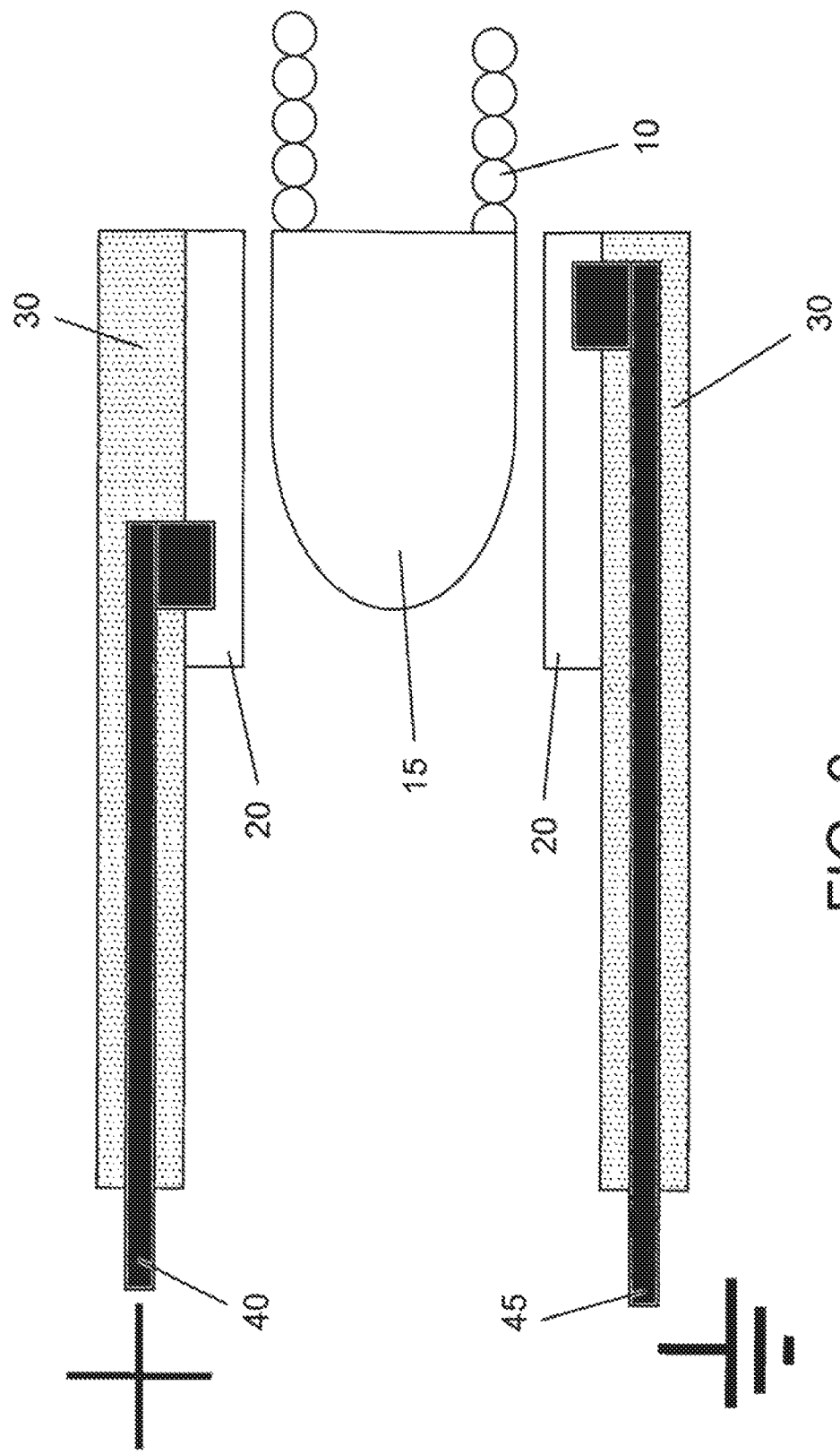
FIG. 2 is a partial cross-section, side view depicting the exemplary vaso-occlusive assembly of FIG. 1 and showing the electroactive polymer detachment mechanism in the configuration that does not engage the vaso-occlusive device.

FIG. 2 is a side and partial cross-section view of the vaso-occlusive assembly of FIG. 1 after changing configuration of the electroactive polymer by application or removal of electrical current. For electroactive polymers that contract upon application of electrical energy, is hydration and ion transport around the electroactive polymer shrinks the polymer, thereby reducing its thickness. Likewise, for electroactive polymers that expand upon application of electrical energy, the polymer will contract when the electrical current is removed. In either case, the shrunken polymer 20 releases its hold on the coil 10, and allows withdrawal of the delivery device 30 while leaving the coil 10 in the vessel.

Figure 3A:
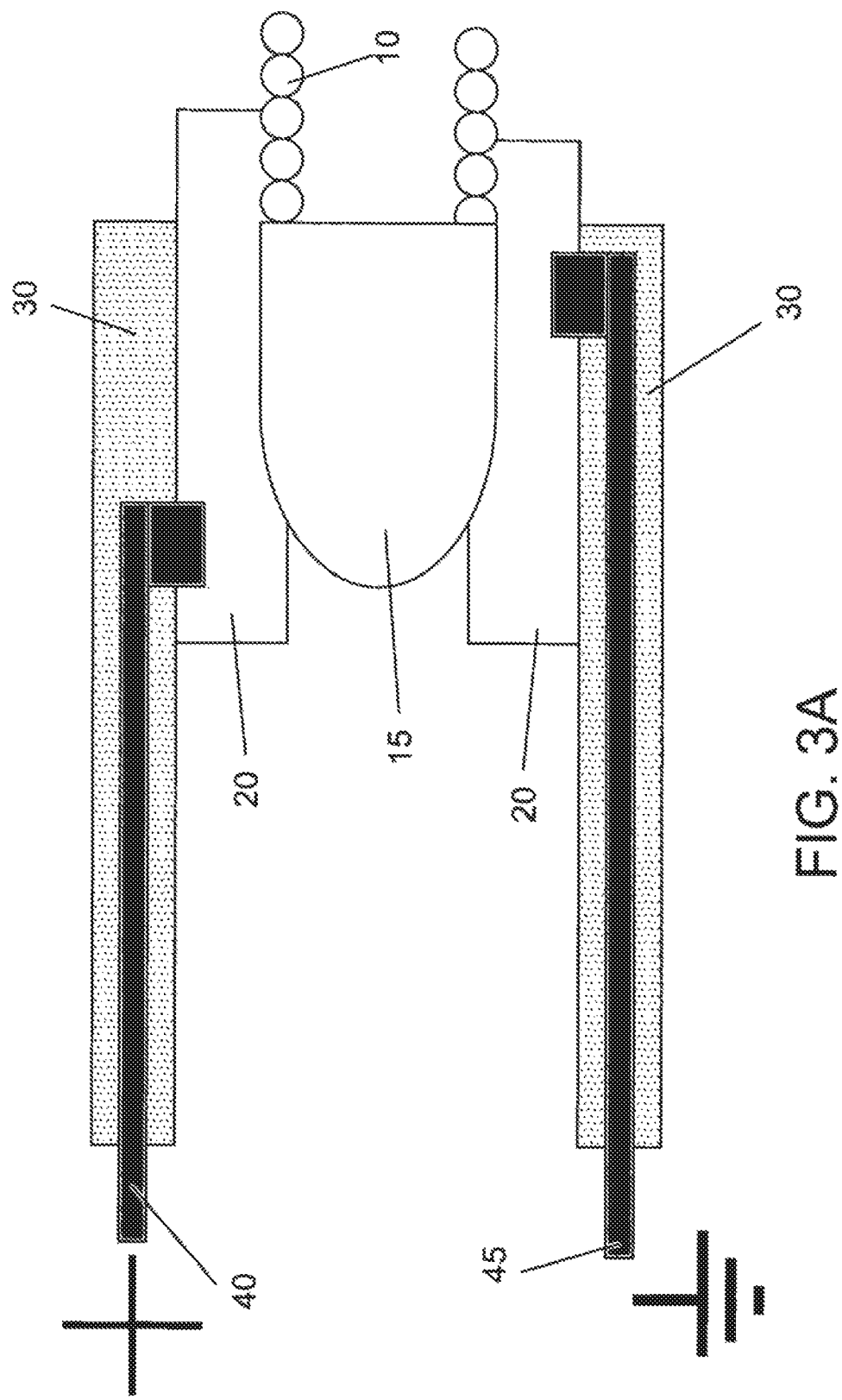
FIG. 3A, FIG. 3B and FIG. 3C, are partial cross-section, side views depicting another exemplary vaso-occlusive as described herein, in which the electroactive polymer extends beyond the distal end of the delivery device.
Figure 3B:
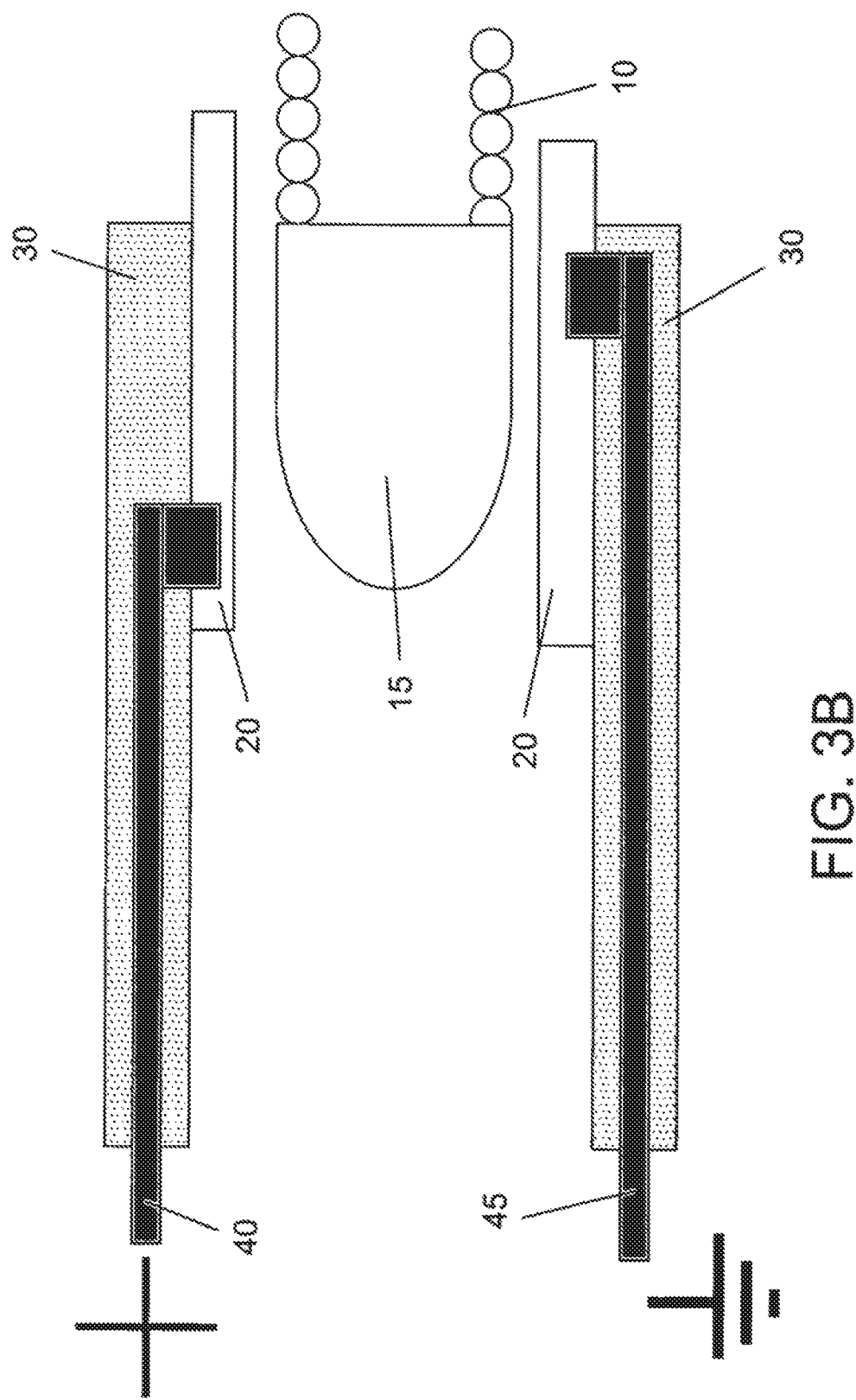
Figure 3C:
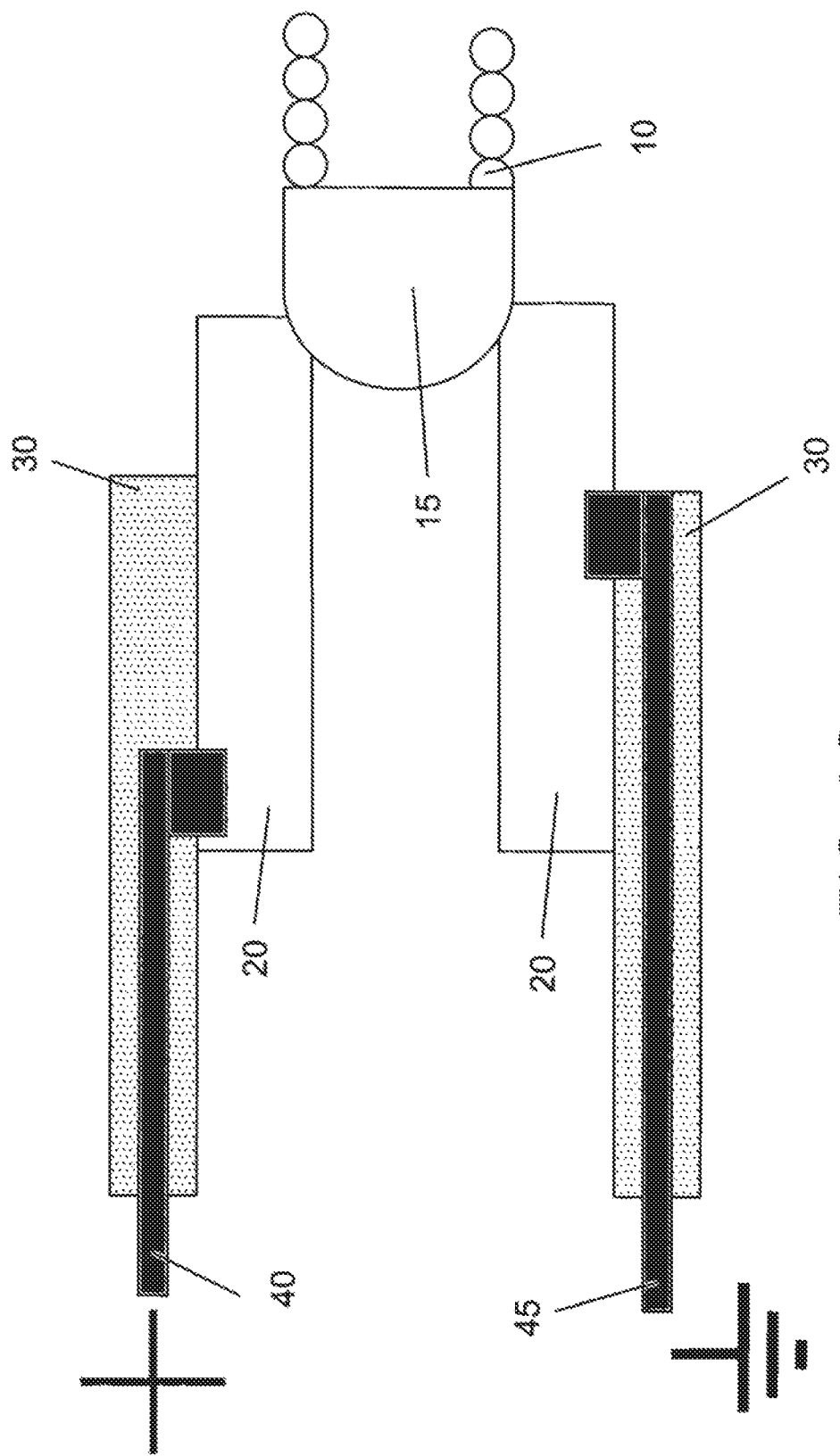

FIG. 3, panels FIG. 3A to FIG. 3C, show another exemplary assembly in which the electroactive polymer material 20 extends beyond the delivery device 30. FIG. 3A shows a cross-section of the assembly in the engaged configuration. FIG. 3B is a cross-section view of the embodiment of FIG. 3A upon changing the configuration of the electroactive polymer by application or removal of electrical energy. The inner diameter of the tube created by the electroactive polymer 20 increases and, in addition, the axilinear length of the polymer increases. This minimizes coil movement during detachment. FIG. 3C shows the detachment mechanism in an intermediate activated state in which the thickness of the electroactive polymer 20 is partially shrunk and the polymer can aid in coil 10 positioning and/or pushing.

FIG. 4 shows an exemplary embodiment in which a structural element (e.g. ball) 70 is secured at or near the proximal end of the coil 10 and extends through the electroactive polymer 20. The ball 70 is placed inside the delivery tube and held in place by the electroactive polymer 20. When the configuration of the electroactive polymer 20 is changed via anode 75 and cathode 77, the electroactive polymer 20 changes configuration sufficiently to produce a luminal gap large enough for the delivery tube to be withdrawn over the ball 70. This design may provide improved tensile strength because the tensile load surface is loaded normally instead of in shear.

It will be apparent that the structure may be secured to the coil at any location and by any suitable means, for example, gluing, soldering, welding, etc. Furthermore, any structural element can be used, including, for example, ball, rings, hooks and the like.

FIG. 5 shows yet another design using multiple layers of electroactive polymer 20. In this design, the inner and outer surfaces of the proximal end of the coil 10 are surrounded by electroactive polymer 20. Also shown are delivery tube 30, anodes 75, and cathodes 77.

FIGS. 6A to 6F are cross-section views of detachment mechanisms comprising an electroactive polymer and additional materials. Shown in FIG. 6A are configurations in which the electroactive polymer is layered with other materials that fill space and/or provide desirable adhesion properties to the delivery device or coil. Other configurations, for example, mixtures of materials and overlapping regions of different materials are also contemplated. Non-limiting examples of other materials include metal and/or polymers (e.g., PET).

FIGS. 6A to 6C depict embodiments in which the electroactive polymer-comprising structure is a ring or tube-like shape. FIG. 6A shows a cross-section view of an exemplary detachment mechanism including an inner electroactive polymer inner layer 20, an outer core (e.g., tube) layer 85 and a middle layer of filler polymer 80 sandwiched between the electroactive polymer 20 and the outer tube layer 85. FIG. 6B shows a cross-section view of another exemplary detachment mechanism including an inner filler polymer layer 80, an outer tube layer 85 and a middle layer of electroactive polymer 20 sandwiched between the filler polymer 80 and the outer core layer 85. FIG. 6C shows a cross-section view of another exemplary detachment mechanism including an inner electroactive polymer layer 20, an outer core or tube layer 85 and a middle layer of filler material 85 sandwiched between the electroactive polymer 20 and the outer core layer 85. FIG. 6C also illustrates how the detachment mechanism need not be a solid annulus, but can include one or more slots 87 or other discontinuous formations that may allow for more uniform and/or facile expansion and contraction of the electroactive polymer.

FIGS. 6D through 6F depict embodiments in which detachment mechanism comprises a core wire instead of tube. In particular, FIG. 6D shows a cross-section view of an exemplary detachment mechanism comprising a core wire 85 surrounded by a layer of filler material 80, which in turn is surrounded by an outer layer of electroactive polymer 20. FIG. 6E shows the detachment mechanism of FIG. 6D further comprising slots 87 in the electroactive polymer 20 and filler material layers 80. FIG. 6F shows a cross-section view of an exemplary detachment mechanism comprising a core wire 85 surrounded by a layer of electroactive polymer 20, which in turn is surrounded by an outer layer of filler material 80. Also shown are slots 87 in the electroactive polymer 20 and filler material layers 80.

FIG. 7 shows a cross-section view of an exemplary assembly described herein which the deployment tube 30 comprises one or more apertures 95 in the sidewalls of the delivery tube. Also shown are electroactive polymer 20, which forms a ring in the inside of the delivery tube 30, electrodes 90 and implantable device 10. The apertures in the sidewalls allow for both inflow of electrolytes (e.g., blood) and outflow of electrolytes that can be infused into the lumen of the delivery device by the operator. Non-limiting examples of suitable electrolytes include saline, phosphate buffered saline and the like.

FIGS. 8 and 9 show exemplary cross-section views of electroactive polymer 20 configurations included apertures or slots 97 therein. The use of non-solid electroactive polymers provides more surface area for the diffusion of electrolytes which further increases the efficiency of the applied electrical energy in changing the configuration of the polymer and releasing the implantable device.

FIG. 10A is a side, cross-section view of an exemplary vaso-occlusive assembly in which a detachment mechanism comprising a ring-shaped electroactive polymer 20 disposed to fit within the lumen of the implantable embolic coil 10 and mounted on the distal end of dual conductor electrode 32, with positive 35 negative 37 electrodes within electroactive polymer ring 20. The dual conductor electrode 32, may be coaxial or a twisted pair of conductors. Also shown in FIG. 10A is marker coil 50, including radio-opaque (e.g., platinum) proximal coil winds 55. The electroactive polymer 20 expands upon application of electrical current and is shown in the un-activated state in which it has a diameter less than the inner diameter of the embolic coil 10.

FIG. 10B shows the assembly of FIG. 10A in the activated state. The diameter of the electroactive polymer 20 increases upon application of electrical energy to hold the coil 10 in place, for example against a stopper and/or marker coil 50.

When the delivery device comprises a marker or stopper coil, it can be of the same or different diameter than the implantable device. In certain embodiments, the stopper coil has a slightly smaller inner diameter than the implantable coil such that when the coils are axially aligned they contact each other but create a ridged area at their junctions. In the engaged coils were of the same diameter.

In embodiments in which the electroactive polymer expands upon the application of electrical energy, the implantable device is positioned within the delivery device and the electroactive polymer is energized to keep the coil in the desired position. For example, in the design shown in FIG. 10B, the electroactive polymer ring is inserted into the lumen of the main coil and energized. The device is then introduced into the access delivery device (e.g., microcatheter). Upon achieving the desired positioning within the aneurysm, the coil is detached by de-energizing the electroactive polymer. These embodiments, allows the option of the supplying long lengths of uncut embolic coils to the surgeon. The surgeon can trim the coils to the desired length and mount them on the delivery device to deploy the coils. Delivery devices can be reused multiple times so as, the lumen remains sufficiently clear for insertion. Furthermore, these embodiments minimize the possibility of false or premature detachment of the coil.

FIG. 11 shows another embodiment in which the electroactive polymer shrinks (reduces diameter) upon application of electrical current. FIG. 11A is a side, cross-section of an exemplary vaso-occlusive assembly in an un-activated (expanded) state. A detachment mechanism comprising an electroactive polymer 20 is disposed to fit within the lumen of the implantable dual diameter embolic coil 10 and mounted on the distal end of dual conductor electrode 32, with positive 35 negative 37 electrodes. The dual conductor electrode 32, may be coaxial or a twisted pair of conductors. Also shown in FIG. 11A is marker coil 50, including radiopaque (e.g., platinum) proximal coil winds 55 and stopper bands 57. FIG. 11B shows the assembly of FIG. 11A in the activated state. The diameter of the electroactive polymer 20 decreases upon application of electrical energy to release the embolic coil 10 into the desired location in the vessel.

FIGS. 12 and 13 show side views of still other exemplary embodiments in which the detachment mechanism 70 is configured as a composite (layered) strip 60. FIG. 12A shows the composite strip in the release position and FIG. 12B shows the mismatch in expansion of the different layers in the activated position. FIG. 13A shows the composite strip in the release position and also shows a band 77 which may be used to keep the layers of the strip in contact. FIG. 13B shows the composite strip of FIG. 13A upon activation (electrical current or heat) which causes different deflection of the layers of the strip.

Figure 14B:
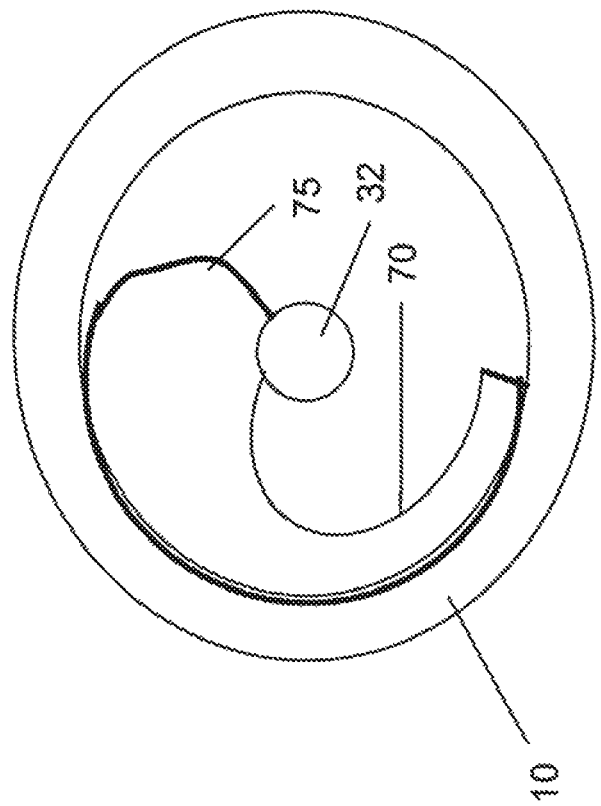
FIG. 14A and FIG. 14B are cross-section views of an exemplary detachment mechanism comprising a bilayer strip as shown in FIGS. 12 and 13, wound into a spiral shape and inserted into the lumen of an implantable device.
Figure 14A:
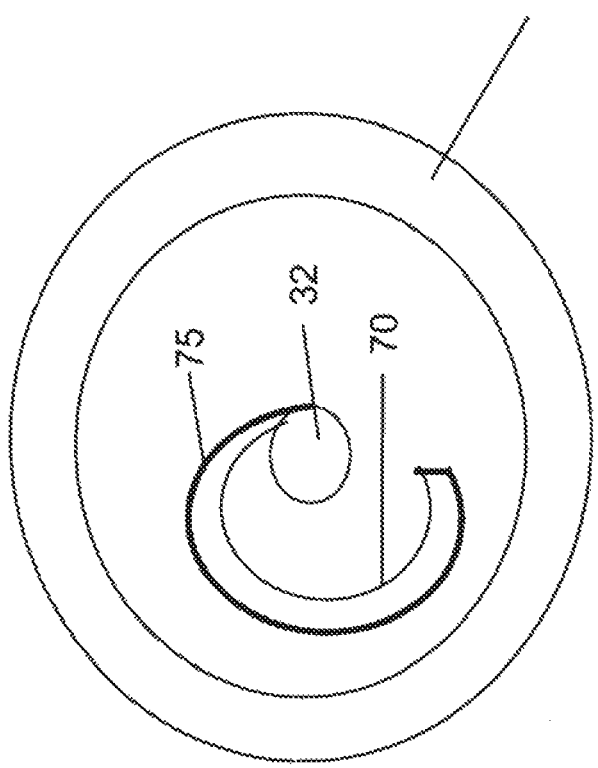

FIG. 14A is front, cross-section view of a composite strip as shown in FIGS. 12 and 13 wound into a spiral shape and positioned within the lumen of an implantable coil 10 in the released configuration. FIG. 14B shows the assembly of FIG. 14A in the engaged configuration, namely when the layered strip engages the inner surface of the implantable device 20.

The layered strip may include an electroactive polymer which expands or contracts upon application of electrical energy. Alternatively, the strip may be comprised of two or more dissimilar metals having disparate thermal expansion coefficients such that, upon a change in temperature, they change shape with relation to the other(s), i.e. deflect, bend, and/or expand. It will be apparent that when an electroactive polymer is used in these strips, the detachment mechanism is operably liked to a source of electrical current. Likewise, if dissimilar metals are used, the strips are operably connected to a heat source.

FIG. 15 depicts a design using layered strips 60 as described above. FIG. 15 depicts a cross-section view of an embodiment in which composite strips 60 extend through the lumen of marker coil 50 and into the lumen of the implantable embolic coil 10 In the expanded (engaged) position the strips 60 may engage the coil 10 directly (e.g., into the winds of the implantable coil) or, alternatively, may engage orifices (e.g., gaps) or structures 80 positioned at appropriate locations within the coil.

FIG. 16 shows yet another design using layered strips 60 within the lumen of an embolic coil 10 and which engage each other via interlocking elements 80 in the released configuration. As shown in FIG. 16, when multiple strips are used within the lumen of the implantable device, they may be offset from each other such that, when they are actuated, they pass each other, which may allow greater range of movement during positioning and deployment. For instance, the strips may be spaced equally around the lumen of implantable device (e.g., 180° apart for two strips; 120° apart for 3 strips, etc.)

As noted above, in any of the embodiments described herein, there may be one or more layers of electroactive polymer. Furthermore, the electroactive polymer can be deposited onto any substrate, for example a metal (e.g., nitinol) or polymer (e.g., urethane). The electroactive polymer can be deposited by any means, for example by coating, gluing, and the like.

In certain embodiments, the assemblies described herein further comprise an element (e.g., band) around the proximal end of the implantable device and/or delivery mechanism to help maintain contact with the electroactive polymer. Non-limiting examples of such elements include thin-walled metal (e.g., stainless steel, nitinol, and/or platinum alloys) and/or polymer (PEEK, PET, polyimide) bands. Alternatively, a region of the coil (e.g., winds of the coil) can be soldered or welded together.

Figure 17:
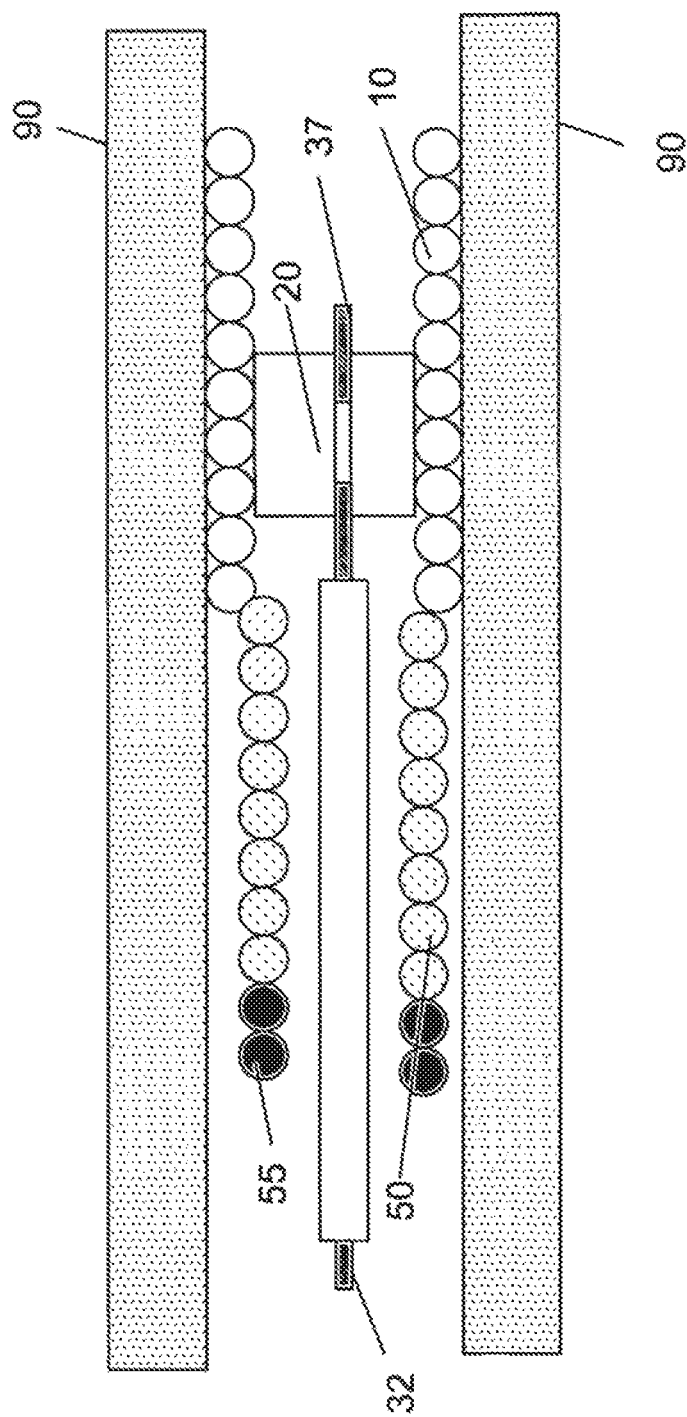
FIG. 17 is a cross-section, side-view of an exemplary assembly as described herein including a delivery device.

FIG. 17 is a side, cross-section view of an exemplary vaso-occlusive assembly in which a detachment mechanism comprising a ring-shaped electroactive polymer 20 is disposed to fit within the lumen of the implantable embolic coil 10 and mounted on the distal end of dual conductor electrode 32, with positive 35 and negative 37 electrodes within electroactive polymer ring 20. Also shown in FIG. 17 is marker coil 50, including radio-opaque (e.g., platinum) proximal coil winds 55 and delivery device 90.

Figure 18:
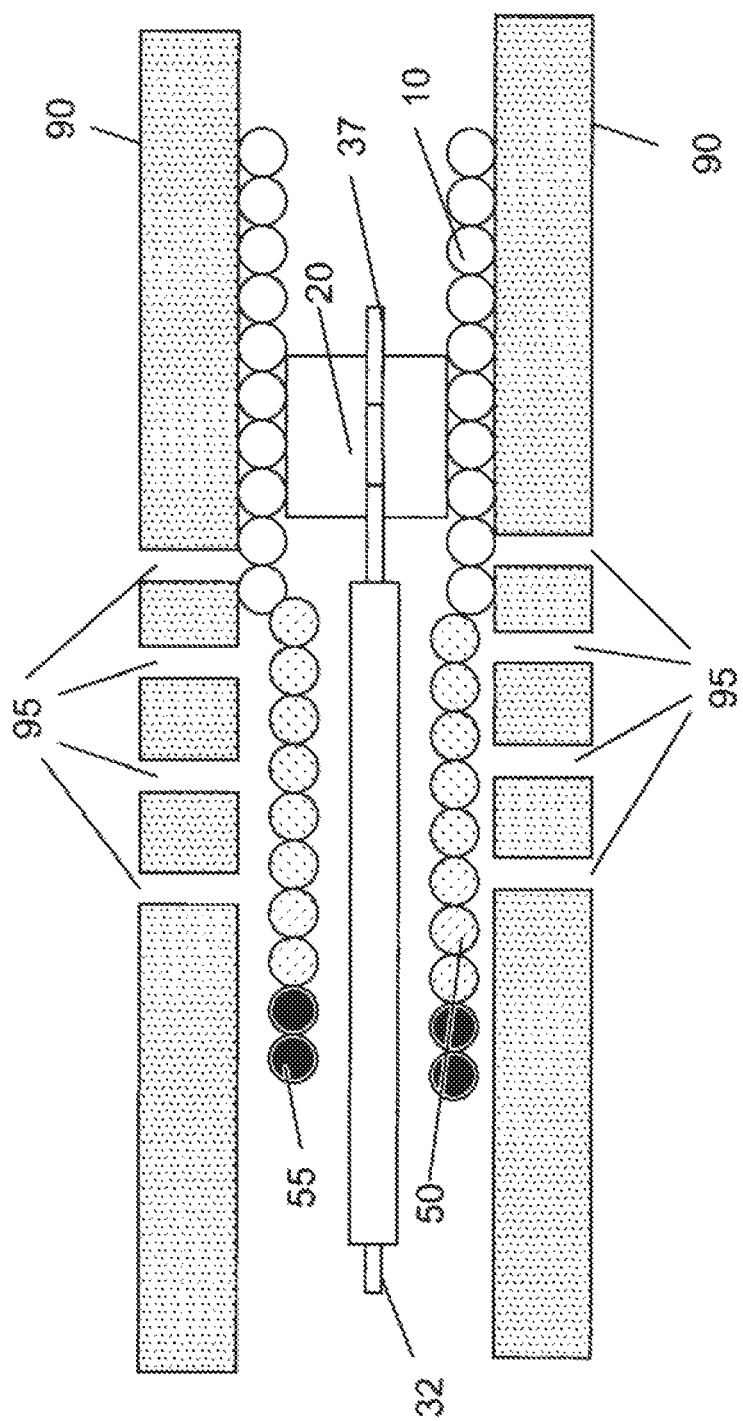
FIG. 18 is a cross-section, side-view of an exemplary assembly as described herein including a delivery device with one or more apertures in the sidewalls.

FIG. 18 is a side, cross-section view of an exemplary vaso-occlusive assembly as shown in FIG. 17 in which the delivery device 90 includes apertures 95 in the sidewalls.

Figure 19:
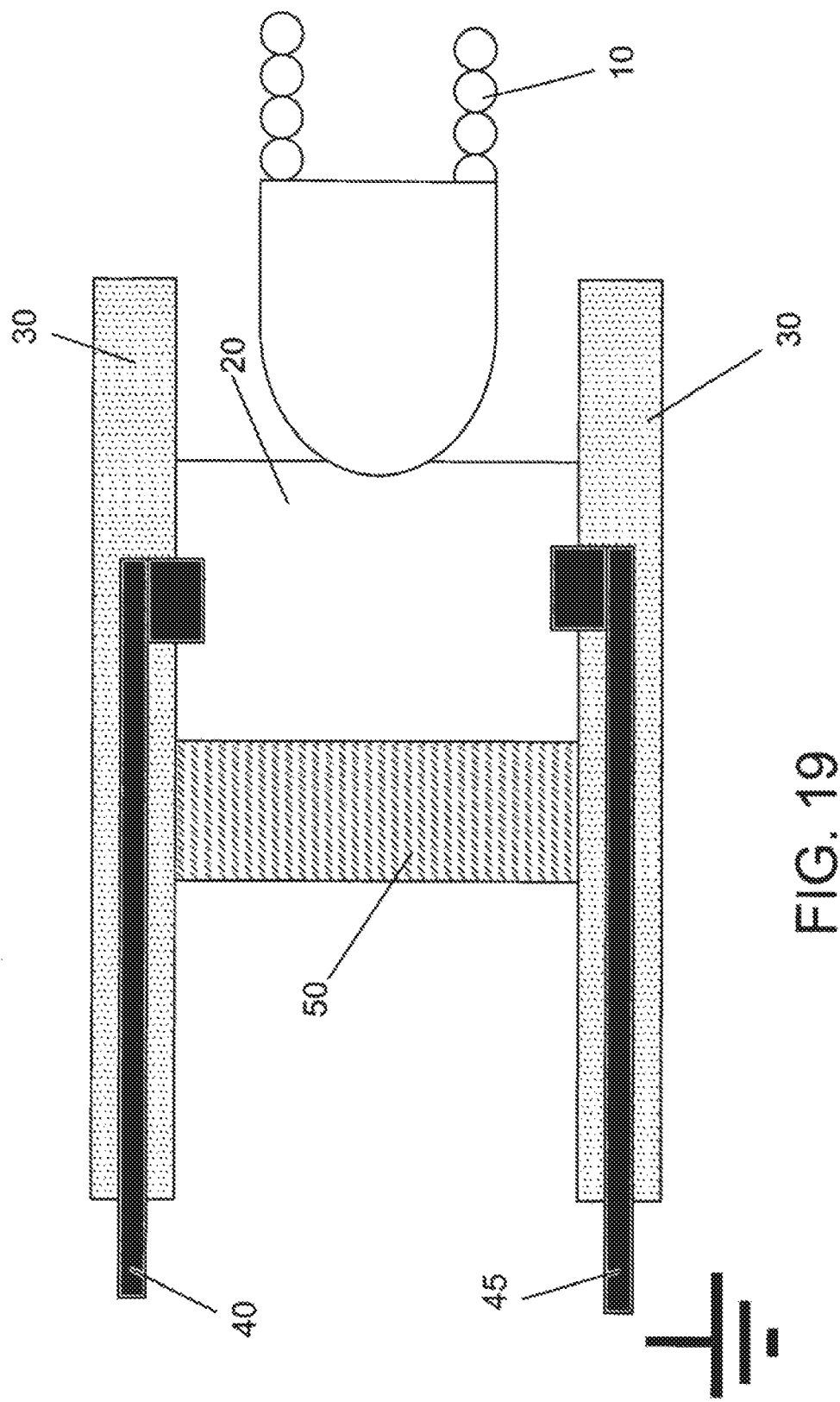
FIG. 19 is a partial cross-section, side view depicting an exemplary vaso-occlusive assembly comprising an electroactive polymer plug in the delivery device. The electroactive polymer plug is shown in the reduced configuration in which the distal boundary of the plug is proximal to the distal end of the delivery device.

FIG. 19 shows a partial cross-section, side-view of another exemplary detachable vase-occlusive assembly as described herein which includes an electroactive polymer plug 20 in the delivery tube 30. The electroactive polymer plug 20 is shown in the reduced volume configuration and contacts the proximal region (tip ball) of vase-occlusive coil 10. Electrodes 40, 45 extend through sidewall of delivery tube 30 and contact electroactive polymer 20. Delivery tube also comprises a stopper 50 proximal to the electroactive polymer plug 20. Stopper 50 prevents expansion of the electroactive polymer proximally within the delivery tube 30. For electroactive polymers that contract upon application of electrical energy, hydration, applied voltage from a power supply, and ion transport around the electroactive polymer shrinks the polymer, thereby reducing the space it occupies in the delivery tube 30.

Figure 20:
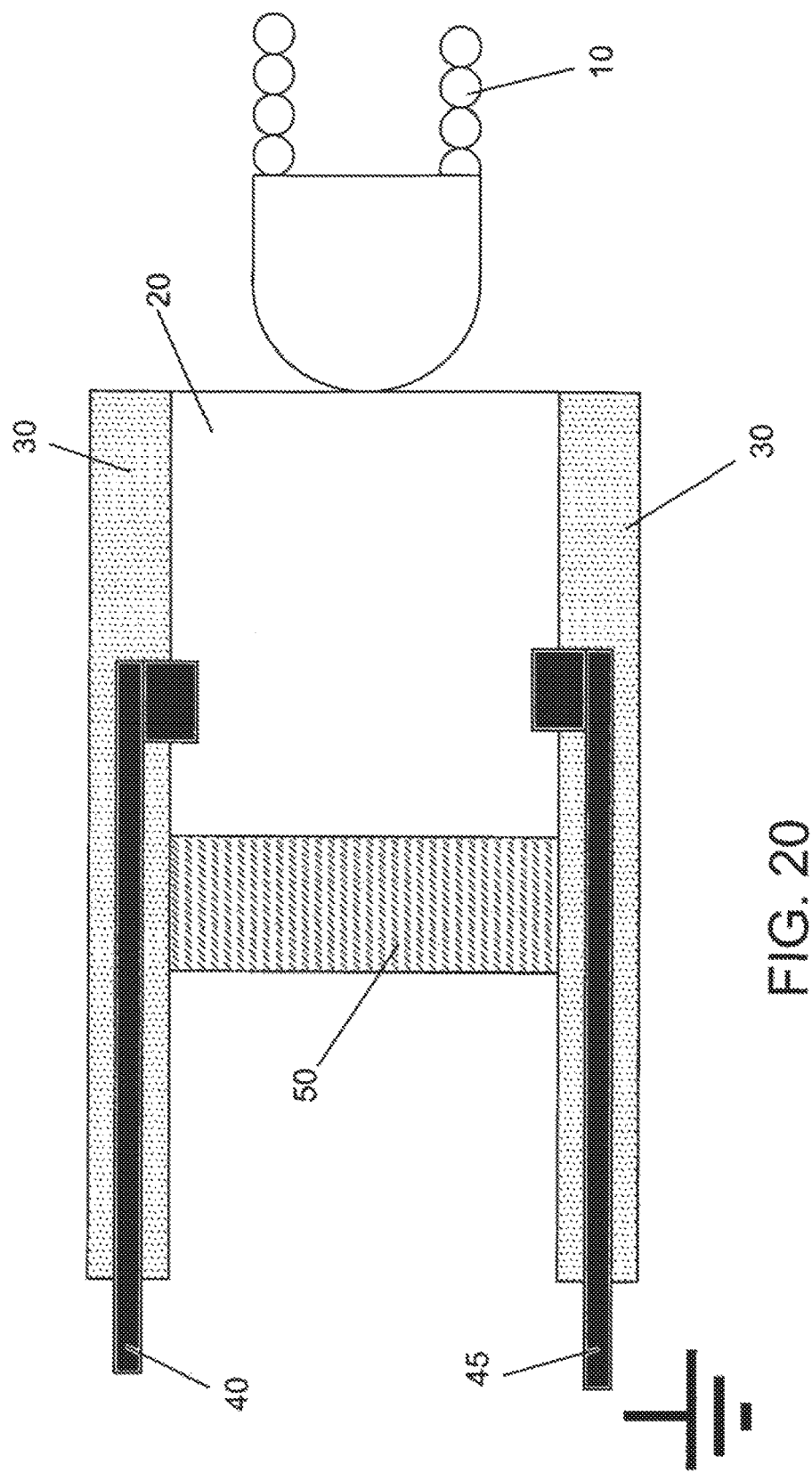
FIG. 20 is a partial cross-section, side view depicting the exemplary vaso-occlusive assembly of FIG. 19 and shows the electroactive polymer plug in the expanded configuration in which the distal boundary of the plug is at or near the distal end of the delivery device, thereby extruding the vaso-occlusive device into the selected site.

FIG. 20 is a side and partial cross-section view of the vaso-occlusive assembly of FIG. 19 after the configuration of the electroactive polymer plug 20 is changed by application or removal of electrical current to its expanded configuration. The polymer plug 20 can expand only distally in delivery tube 30 due to stopper 50 and, accordingly, when expanded pushes coil 10 out of the delivery device and allows withdrawal of the delivery device 30 while leaving the coil 10 in the vessel.

Figure 21:
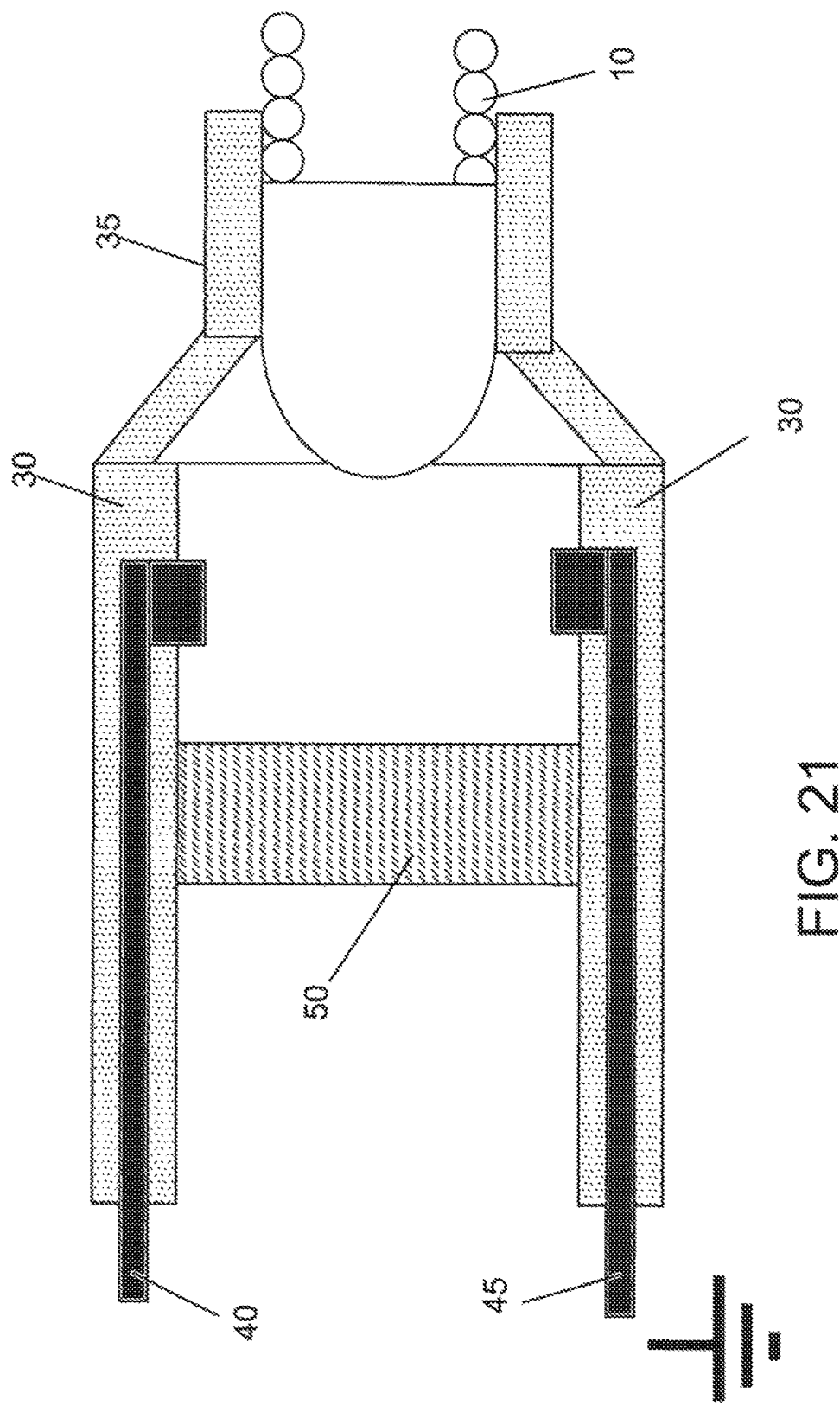
FIG. 21 is a partial cross-section, side view depicting an exemplary vaso-occlusive assembly as described herein. The delivery device includes a collar that is sized to allow for the passage of the vaso-occlusive device. The electroactive polymer plug is shown in the reduced configuration in which the distal boundary of the electroactive polymer plug is proximal to the distal end of the delivery device and collar.

FIG. 21 shows a partial cross-section, side-view of another exemplary detachable vaso-occlusive assembly having an electroactive polymer plug 20 and stopper 50. The electroactive polymer 20 is shown in the reduced volume configuration and contacts the proximal region (tip ball) of vaso-occlusive coil 10. Electrodes 40, 45 extend through sidewall of delivery tube 30 and contact electroactive polymer 20. Delivery tube also comprises a stopper 50 proximal to the electroactive polymer 20. Delivery tube 30 includes a collar 35 that is sized to fit the outer diameter of the vaso-occlusive coil 10.

Figure 22:
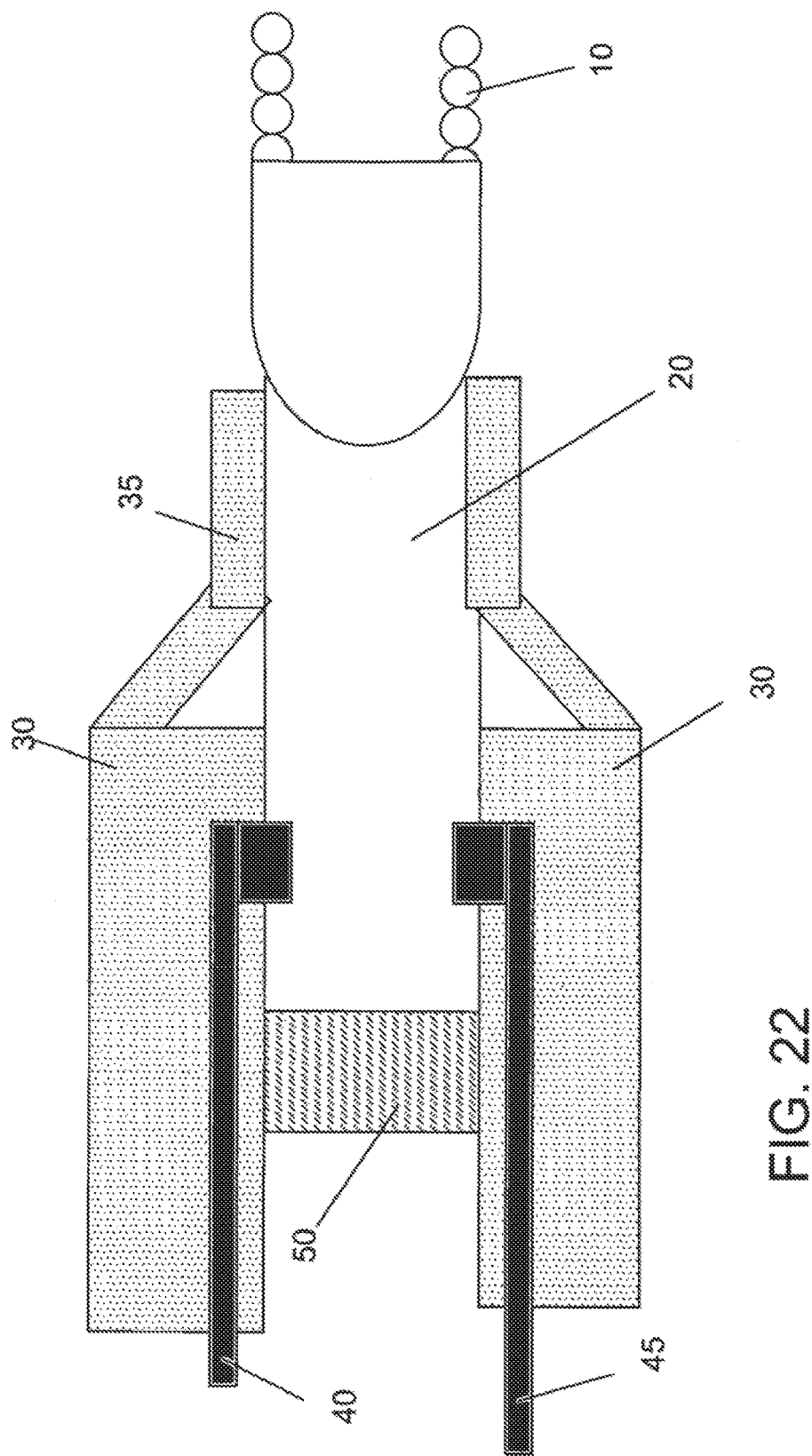
FIG. 22 is a partial cross-section, side view of the assembly shown in FIG. 21 with the electroactive polymer plug in the expanded configuration which causes the plug to extend into the collar and extrude the vaso-occlusive device from the delivery mechanism.

FIG. 22 is a side and partial cross-section view of the vaso-occlusive assembly of FIG. 21 after changing configuration of the electroactive polymer plug 20 (by application or removal of electrical current) to its expanded configuration. The expanded polymer 20 pushes coil 10 out of the collar 35 of delivery device 30 and allows withdrawal of the delivery device 30 while leaving the coil 10 in the vessel.

Figure 23:
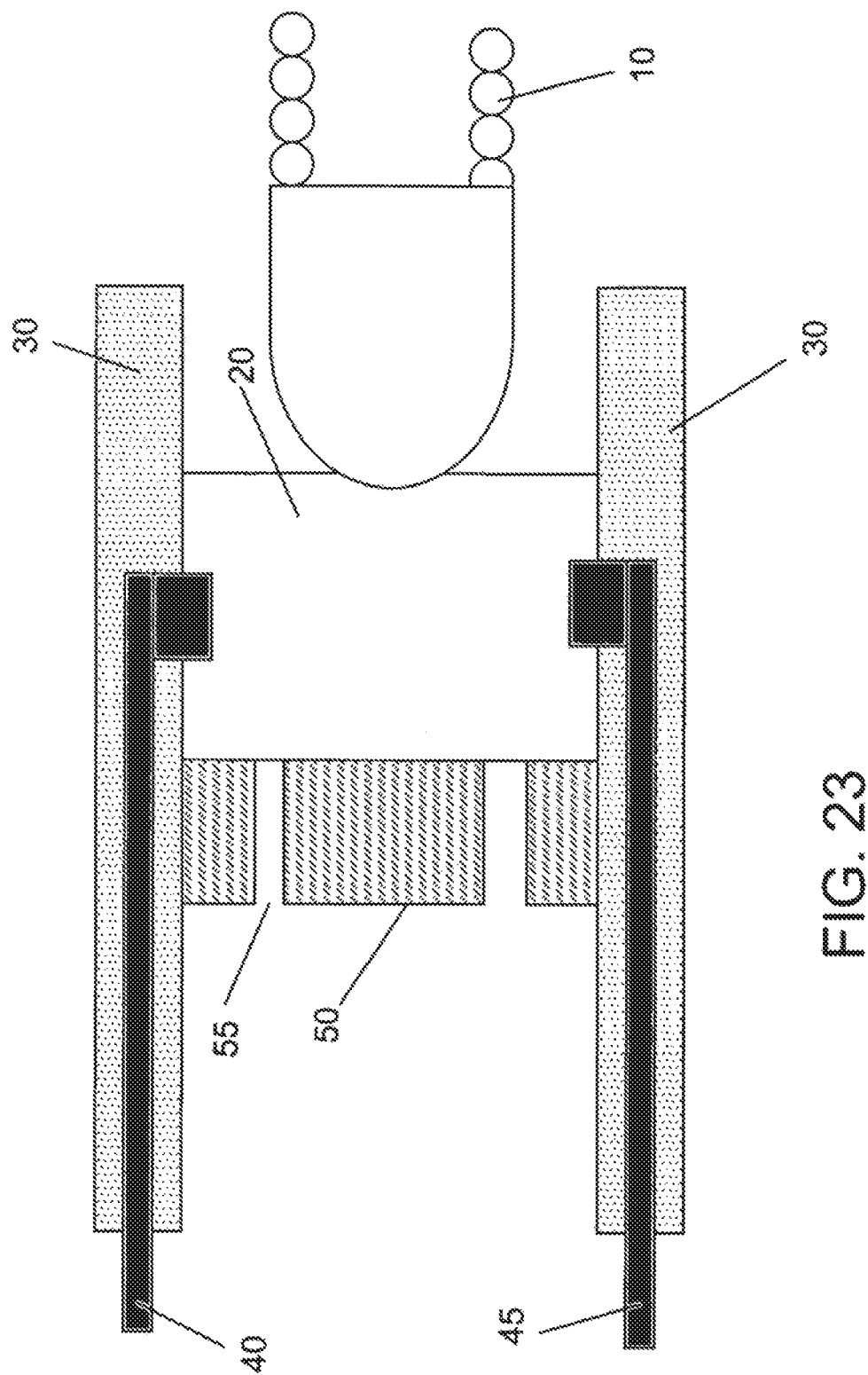
FIG. 23 is a cross-section, side-view of another exemplary assembly as described herein and shows a design having apertures in the proximal stopper to allow flow of electrolytes to the electroactive polymer.

FIG. 23 shows yet another electroactive polymer plug type assembly as described herein in which the stopper 50 comprises apertures 55. The apertures allow electrolytes, for example electrolytic solutions that are infused into the lumen of the delivery tube by the operator, to contact the electroactive polymer 20.

FIG. 23 shows yet another electroactive polymer plug type assembly as described herein in which the stopper 50 comprises apertures 55. The apertures allow electrolytes, for example electrolytic solutions that are infused into the lumen of the delivery tube by the operator, to contact the electroactive polymer 20.

FIG. 23 shows yet another electroactive polymer plug type assembly as described herein in which the stopper 50 comprises apertures 55. The apertures allow electrolytes, for example electrolytic solutions that are infused into the lumen of the delivery tube by the operator, to contact the electroactive polymer 20.

Figure 24:
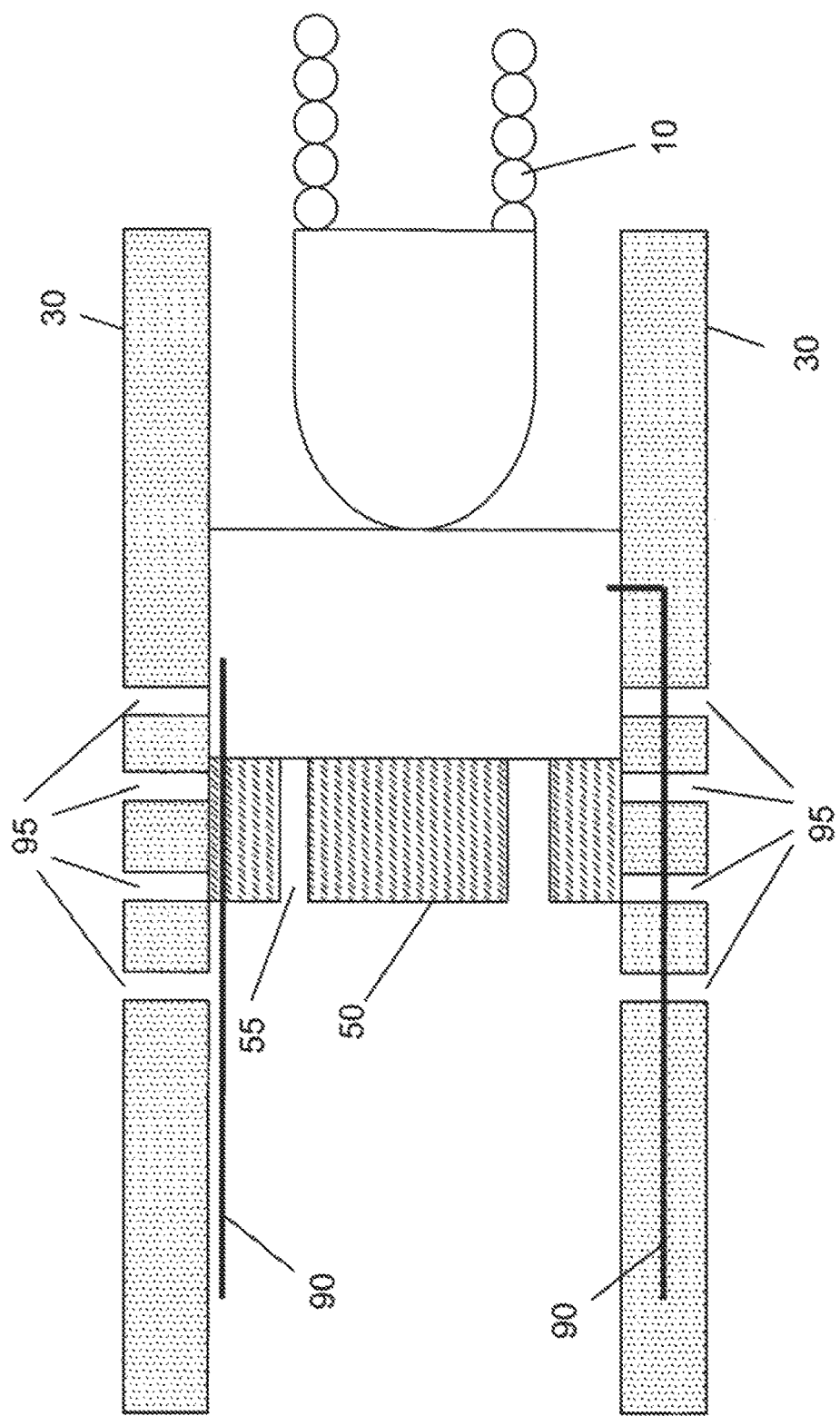
FIG. 24 is a cross-section, side-view of the exemplary assembly shown in FIG. 23 and further depicting a delivery device with one or more apertures in the sidewalls.

FIG. 24 shows a cross-section view of an electroactive plug-type assembly described herein in which the deployment tube 30 comprises one or more apertures 95 in the sidewalls of the delivery tube. Also shown are electroactive polymer 20, stopper with apertures 50, 55, delivery tube 30, electrodes 90 and implantable device 10. The apertures in the sidewalls allow for both inflow of electrolytes (e.g., blood) and outflow of electrolytes that can be infused into the lumen of the delivery device by the operator. Non-limiting examples of suitable electrolytes include saline, phosphate buffered saline and the like.

FIG. 25A shows a side view of another exemplary assembly as described herein in which an electroactive polymer detachment mechanism 20 is wound around a structure 72 at the proximal end of the coil 10. The detachment mechanism 20 may optionally directly contact the coil 10. FIG. 25A shows the electroactive polymer 20 in the unexpanded (smaller diameter) configuration in which the coil 10 is engaged by the detachment mechanism 20. FIGS. 25B and 25C depict the device of FIG. 25A with the electroactive polymer 20 in the expanded configuration which no longer engages the structure 72, thereby releasing the coil 10. As shown, the structure 72 engaged by the electroactive polymer 20 may be attached to the proximal end of the coil 10 (FIG. 25B) or to the distal end of a pusher element, for example a pusher comprising an electrical conductor 32.

Although shown in FIG. 25A-C as a coiled structure 72, it will be apparent that the electroactive polymer 20 may be attached to any shaped structure, for example, a straight solid or hollow tube (optionally surfaced roughened, e.g., by mechanical blasting, grinding or chemical etching). It will also be apparent that the structure 72 may be made of any material (polymer and/or metal), for example the same material as the coil (e.g., platinum alloy). Likewise, the electroactive polymer may take a variety of shapes, for example a ring shape or a helical (spiral) shape as depicted in FIG. 25. Optionally, the electroactive polymer may be disposed on a substrate, for example a thin, flexible polymer such as polyimide or polyester. In addition, one or more loops of the coil may be soldered or welded together, which may reduce stretching during movement of the coil.

FIG. 26A shows a cross-section, side-view of an embodiment in which arm-like structures 73 extending from the proximal region of the coil 10 engage a pusher element 31 in slots containing an electroactive polymer 20 in an unexpanded configuration. FIG. 26B shows the assembly when the electroactive polymer 20 expands and the arms 73 no longer engage the pusher element 31. Pusher element 31 includes an electrical conductor 32 for activation of the electroactive polymer 20. The arms may be made of any material (e.g., polymer and/or metal) and may be integral or attached to the implantable device. Although depicted in FIG. 26 with two arms, more than 2 arms may be employed and may improve tensile strength, for example, 3, 4, 5, 6 or even more arms. The grips may also be of any configuration that engages the arms and may be built into the tubular pusher or may be attached to the distal end of pusher. The pusher can be made from any material, for example nitinol. The pusher body may optionally comprise a metallic hypotube component that is flexible distally; a polymer jacket/liner; and/or a metal reinforced polymer structure. Additional elements, for example, radiopaque markers, may also be included on the pusher element.

Figure 27D:
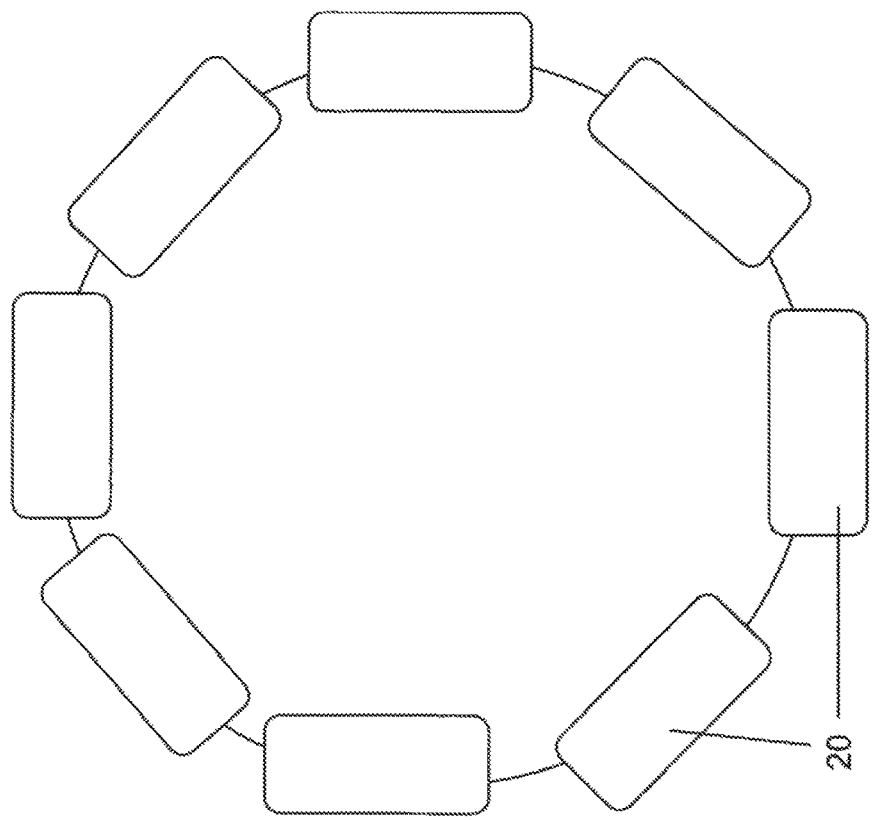
Figure 27C:
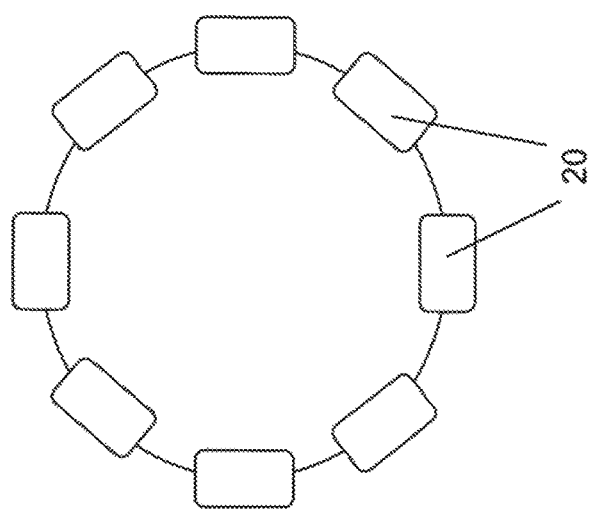

FIG. 27A shows a cross-section, side-view of an embodiment in which the electroactive polymer 20 is a ring attached to the proximal region of the coil 10 and which engages a pusher element 31 in the unexpanded configuration. FIG. 27B shows the assembly when the electroactive polymer 20 expands and the diameter of the ring increases so it no longer engages the pusher element 31 and the coil 10 is detached. Pusher element 31 includes an electrical conductor 32 for activation of the electroactive polymer 20 and optionally includes a slot or groove adapted to fit the ring of electroactive polymer 20. FIG. 27C shows a cross-section of an exemplary electroactive polymer ring 20 may be made up of multiple discontinuous electroactive polymer elements in an unexpanded state. FIG. 27D shows the electroactive polymer ring structure 20 of FIG. 27C after linear expansion of the electroactive polymer ring.

FIGS. 28 to 30 show cross-section, side-views of additional embodiments in which the implantable device 10 engages a pusher element 31 when the electroactive polymer 20 is in a contracted position. FIG. 287A shows a ball 73 structure on the proximal end of the coil 10 20 engaged by arms 74 when the electroactive polymer 20 is contracted. FIG. 28B shows release of the ball joint when the electroactive polymer 20 is expanded. FIG. 29A shows an assembly where arms 74 on the pusher element 31 engage a ring structure 73 on the coil 10 when the electroactive polymer 20 is in the contracted position. FIG. 29B shows the assembly when the electroactive polymer 20 expands and the arms 74 no longer engage the ring 73. FIG. 30A shows an assembly where the unexpanded electroactive polymer 20 engages a structure 73, 73a on the proximal end of the coil 10 embodiment distal to the enlarged end 73 of the structure. FIG. 30B shows the assembly upon expansion of the electroactive polymer 20 to release the structure 73, 73a and attached coil 10. FIG. 30C is a top view of the structure 73, 73a extending from the implantable coil and electroactive polymer 20 in unexpanded configuration and shows the structure shown in FIG. 30C with the electroactive polymer panels in the expanded configuration.

FIG. 31 shows an embodiment that includes a coupling receiver 79 extending from a delivery device 30. As shown in FIG. 31A, the coupling receiver 79 comprises an electroactive polymer or electroactive strip (e.g. electroactive wire) 20 that engages a coupling device 73 extending from the implantable device 10 when the electroactive polymer/ strip 20 is in an expanded configuration (e.g., activated). The electroactive polymer 20 releases the coupling device 73 in the unexpanded (e.g., deactivated). The coupling receiver 79 and coupling device 73 may be of any configuration. Similarly, the electroactive polymer 20 may a ring-like structure with or without channels therein, for example as shown in FIG. 9B. In other embodiments, the device includes an. electroactive wire, for example a nickel titanium shape memory or superelastic wire that responds to heat activation via electric current (see, also, FIGS. 12 and 13). Designs with a coupling mechanism may enhance the ability of the operator to reposition and manipulate the device during implantation. For example, the delivery device and detaching device may be able to rotate as much as 1 to 1 torque and/or independent of each other.

FIG. 32 shows a compression (hydraulic) type detachment mechanism including a tubular pusher element made up of an incompressible material 31 and an electroactive polymer 20. Typically, the incompressible material 31 also acts as an electrolyte. The coil 10 is engaged with the tubular pusher element when the electroactive polymer is in the unexpanded configuration, for example by an interference fit. FIG. 32A shows the assembly when the electroactive polymer 20 is in the unexpanded configuration. Upon volumetric expansion of the electroactive polymer 20 the pressure inside the tubular pusher increases until the coil 10 is released.

Figure 33A:
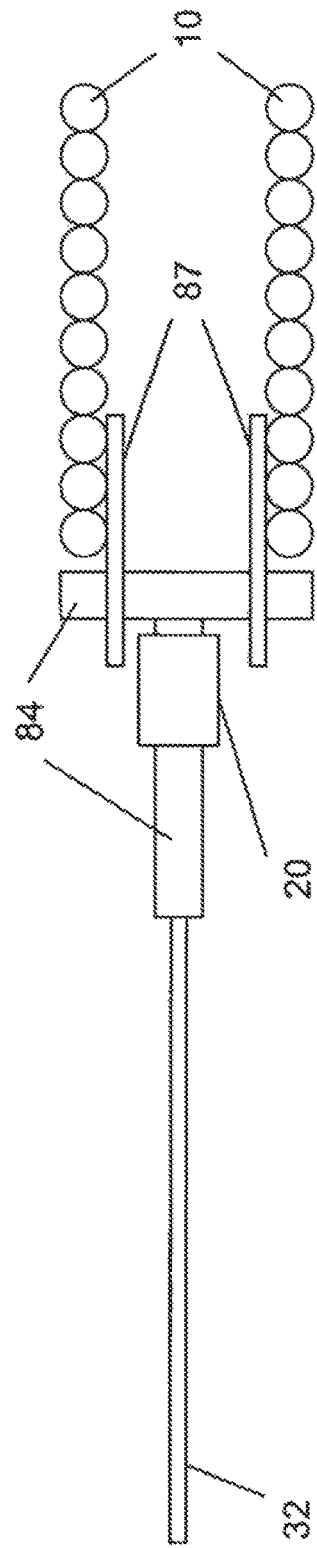
FIG. 33A and FIG. 33B, are cross-section, side-views showing another exemplary variation in which the implantable device engages a T-bar structure when the electroactive polymer is in the contracted position (FIG. 33A). Upon expansion of the electroactive polymer, the implantable device is released (FIG. 33B).
Figure 33B:
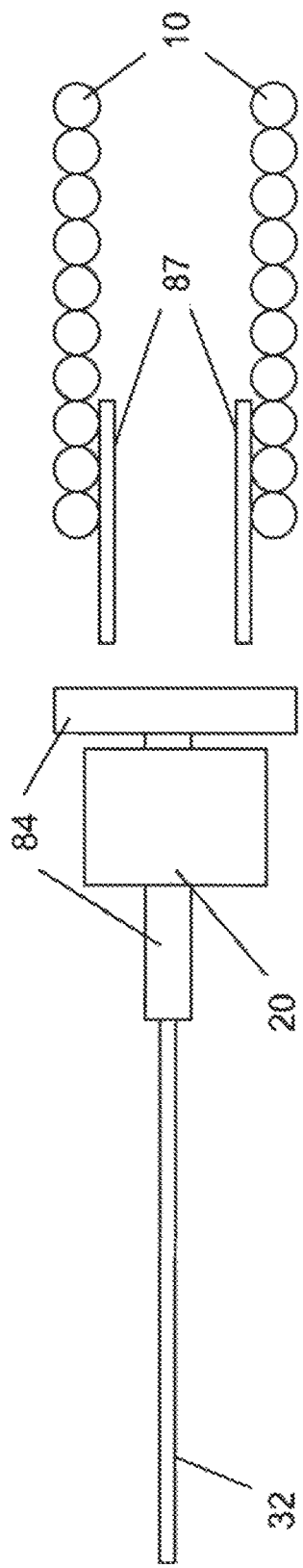

FIG. 33A shows a cross-section, side-view of an embodiment in which a T-bar structure 84 engages fin-like structures 87 attached to the implantable coil 10. Also shown is an electrical conductor 32 for activation of the electroactive polymer 20. Typically, the fin-like structures 87 are attached to the implantable device (e.g., the interior of a coil) and include apertures through which the T-bar structure 84 extends. An electroactive polymer 20 is disposed on the T-bar 84 such that, in the contracted position, the T-bar 84 engages the fin-like structures 87 extending from the implantable device 10. FIG. 33B shows the assembly when the electroactive polymer 20 expands causing the fin-like structures 87 to extend beyond the ends of the T-bar 84 so that the T-bar 84 no longer engages the device 10.

Figure 34A:
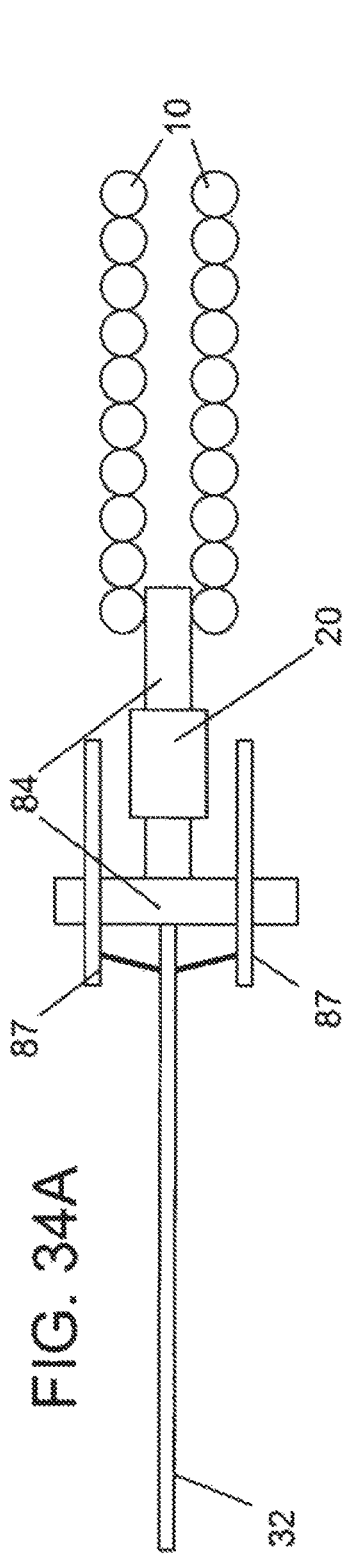
FIG. 34A and FIG. 34B, are cross-section, side-views showing another exemplary variation in which the implantable device engages a T-bar structure when the electroactive polymer is in the contracted position (FIG. 34A). Upon expansion of the electroactive polymer, the implantable device is released (FIG. 34B).
Figure 34B:
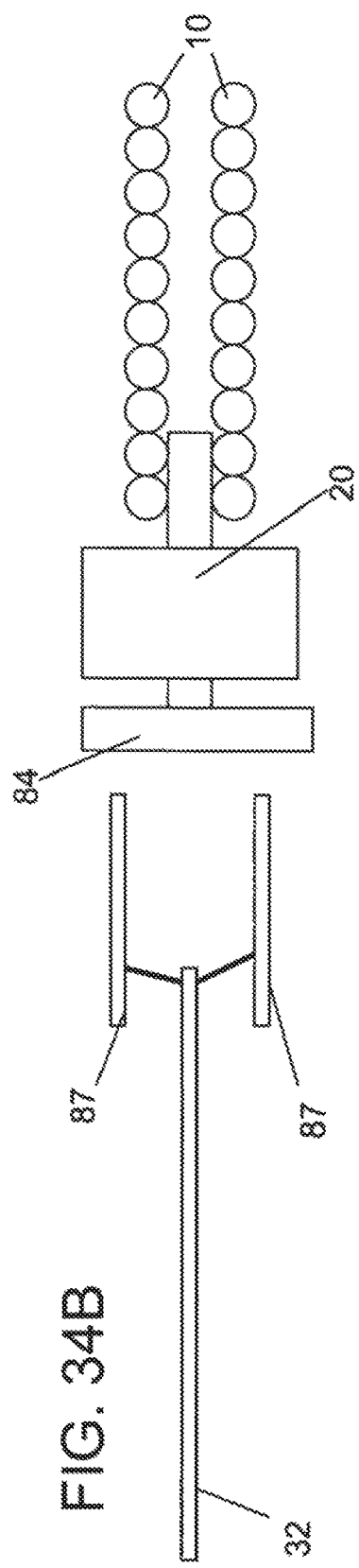

FIGS. 34A and 34B show an alternative embodiment, in which the T-bar structure 84 is attached to the implantable device 10 and engages structures 87 proximal to the implantable device 10. As with the embodiment shown in FIG. 33, expansion of the electroactive polymer 20 pushes the fins off the T-bar and releases the implantable device 10 from the pusher element (FIG. 34B).

The T-bar may not be a single T in that any number of posts can be used, for example, 1, 2, 3, 4, 5 or even more posts can be used. In a preferred embodiment, the T-bar includes 2 posts.

Furthermore, the T-bar and structures (e.g., fin-like structures) it engages maybe made of any material (e.g., polymer and/or metal). In certain embodiments, the fin-like structures comprise platinum. In other embodiments, the T-bar comprises platinum, nitinol, stainless steel and/or polyimide and can be electrochemically etched or formed by bending segments of wire. The fin-like structures or T-bar may be attached to the implant by any suitable means, including but not limited to soldering, welding, adhesives, etc. An optional collar may be placed around the finds and/or T-bar to reduce or prevent pivoting of the fins about the T-bar structure.

FIG. 35 shows an exemplary embodiment in which a structural element (e.g. sphere or ovoid ball like structure) is secured at or near the proximal end of the coil 10 and into delivery device 30 (e.g., hypotube) where it is held in place by electroactive polymer 20 in an expanded configuration. When the polarity of current applied to the electroactive polymer 20 is reversed via electrodes 32, the polymer expands linearly such that it no longer secures the device 10 within the delivery device 30. Also shown is optional groove or slot in the delivery device 37 that provides a seating location of the proximal coil ball.

In any of the embodiments described herein, the electroactive polymer 20 can be disposed directly on the delivery device or on a flexible substrate 38, for example a flexible substrate that deflects when the electroactive polymer 20 disposed therein is activated/unactivated by electrical current (see, e.g., description above regarding FIGS. 13A and 13B).

The devices described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, occlusive devices (and/or additional components) described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g. vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared and/or flushed with an electrolyte solution.

Once the selected site has been reached, the vaso-occlusive device is extruded using a pusher-detachment mechanism as described herein and released in the desired position of the selected site.

Modifications of the procedure and. vaso-occlusive devices described above, and the methods of using them in keeping with this disclosure will be apparent to those having skill in this mechanical and surgical art. These variations are intended to be within the scope of the claims that follow.

What is claimed is:

1. An assembly, comprising:
   an implantable device that includes a structure having a plurality of adjacent windings extending therefrom; and
   a detachment mechanism that includes a first electroactive polymer and a second electroactive polymer each configured to reversibly engage the structure between two of the adjacent windings;
   wherein the first and second electroactive polymers move from an expanded configuration to an unexpanded configuration such that the first and second electroactive polymers overlap each other, upon application of heat or electrical energy, to release the implantable device.

2. The assembly of claim 1, the detachment mechanism further comprising an energy source, wherein the first and second electroactive polymers are in direct contact with the energy source.

3. The assembly of claim 1, the detachment mechanism further comprising an energy source, wherein the first and second electroactive polymers are not in direct contact with the energy source.

4. The assembly of claim 1, wherein the first and second electroactive polymers in the unexpanded configuration are substantially disengaged from the structure of the implantable device.

5. The assembly of claim 1, wherein the implantable device is a vaso-occlusive coil.

6. A method of delivering an implantable device, comprising:
   introducing an assembly into a lumen of a patient, the assembly comprising:
      an implantable device that includes a structure having a plurality of adjacent windings extending therefrom; and
      a detachment mechanism that includes a first electroactive polymer and a second electroactive polymer each configured to reversibly engage the structure between two of the adjacent windings;
      wherein the first and second electroactive polymers move from an expanded configuration to an unexpanded configuration such that the first and second electroactive polymers overlap each other, upon application of heat or electrical energy, to release the implantable device; and
   applying heat or electrical energy to the first and second electroactive polymers to release the implantable device.

7. The method of claim 6, wherein the lumen is a vessel and the implantable device when released at least partially occludes an aneurysm within the vessel of the patient.

8. The method of claim 6, wherein the implantable device is a vaso-occlusive coil.

9. The method of claim 6, wherein the first and second electroactive polymers move from an unexpanded configuration to an expanded configuration, upon the application of heat thereto.

10. The method of claim 9, further comprising an energy source, wherein the first and second electroactive polymers are in direct contact with the energy source.

11. The method of claim 9, further comprising an energy source, wherein the first and second electroactive polymers are not in direct contact with the energy source.

12. The method of claim 9, wherein the first and second electroactive polymers in the unexpanded configuration are substantially disengaged from the structure of the implantable device.

13. The method of claim 6, further comprising an energy source, wherein the first and second electroactive polymers are in direct contact with the energy source.

14. The method of claim 6, further comprising an energy source, wherein the first and second electroactive polymers are not in direct contact with the energy source.

15. The assembly of claim 1, wherein the detachment mechanism further comprises an elongate tubular member about the first and second electroactive polymers; and
   wherein the first and second electroactive polymers reversibly engage the structure within the elongate tubular member.

16. The assembly of claim 1, wherein the detachment mechanism further comprises an elongate tubular member about the first and second electroactive polymers; and
   wherein the first and second electroactive polymers reversibly engage the structure outside of the elongate tubular member.

17. The assembly of claim 1, further comprising a gap between the two of the adjacent windings, and wherein the first and second electroactive polymers reversibly engage the gap.

18. The assembly of claim 1, wherein the detachment mechanism further comprises an elongate tubular member about the first and second electroactive polymers; and
   wherein the first and second electroactive polymers reversibly engage the structure such that the structure is pushed against the elongate tubular member in the expanded configuration.

19. The assembly of claim 1, wherein the detachment mechanism further comprises an elongate tubular member about the first and second electroactive polymers, the elongate tubular member having an aperture configured for a flow of electrolytes therethrough.

* * * * *